(12) United States Patent
Beckman et al.

(10) Patent No.: US 8,029,774 B2
(45) Date of Patent: Oct. 4, 2011

(54) WOUND HEALING POLYMERIC NETWORKS

(75) Inventors: Eric J. Beckman, Aspinwall, PA (US); Stephen F. Badylak, Pittsburgh, PA (US); Alan H. Wells, Pittsburgh, PA (US); Jianying Zhang, Pittsburgh, PA (US); Donald Freytes, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 1159 days.

(21) Appl. No.: 11/479,627

(22) Filed: Jul. 1, 2006

(65) Prior Publication Data

US 2007/0014755 A1  Jan. 18, 2007

Related U.S. Application Data

(60) Provisional application No. 60/695,912, filed on Jul. 1, 2005, provisional application No. 60/789,372, filed on Apr. 5, 2006.

(51) Int. Cl.
| | |
|---|---|
| *A61K 31/74* | (2006.01) |
| *A61K 38/39* | (2006.01) |
| *A61K 38/00* | (2006.01) |
| *A61K 47/48* | (2006.01) |
| *A61F 2/00* | (2006.01) |
| *A61P 17/02* | (2006.01) |
| *C08G 63/48* | (2006.01) |
| *C08G 63/91* | (2006.01) |
| *C08L 89/00* | (2006.01) |

(52) U.S. Cl. ............. 424/78.08; 424/426; 514/17.2; 525/54.1

(58) Field of Classification Search ........................ None
See application file for complete search history.

(56) References Cited

U.S. PATENT DOCUMENTS

| 3,800,792 | A | * | 4/1974 | McKnight et al. ............... 602/50 |
| 5,643,783 | A | * | 7/1997 | Olsen et al. ..................... 435/325 |
| 2004/0265951 | A1 | | 12/2004 | Messersmith |
| 2008/0144176 | A1 | * | 6/2008 | Sugimura et al. ............. 359/485 |

FOREIGN PATENT DOCUMENTS

| EP | 0367362 A2 | 5/1990 |
| WO | W09912975 A1 | 3/1999 |
| WO | W02004029137 A2 | 4/2004 |
| WO | W02005002597 A1 | 1/2005 |
| WO | W02005118011 A1 | 12/2005 |
| WO | W02007002318 A2 | 1/2007 |
| WO | W02007005792 A3 | 1/2007 |

OTHER PUBLICATIONS

Lee BP. et al. Biomacromolecules 3:1038-1047, 2002.*
Zhang JY, et al. Biomaterials 21(12):1247-1258, 2000.*
Thomas S, McCubbin, P. "A comparison of the antimicrobial effects of four silver-containing dressings on three organisms", J Wound Care, 2003;12(3)101-107.
Holt KB, Bard AJ, "Interaction of silver(I) ions with the respiratory chain of *Escherichia coli*: an electrochemical and scanning electrochemical microscopy study of the antimicrobial mechanism of micromolar Ag+", Biochemistry 2005;44 (39):13214-13223.
Bragg PD, Rainnie DJ., "The effect of silver ions on the respiratory chain of *E. coli*." Can J Microbiol 1974;20 (6):883-889.
Darouiche RO., "Anti-infective efficacy of silver-coated medical prostheses." Clinical Infectious Diseases, 1999;29 (6):1371-1377.
Chaw KC, Manimaran M, Tay Feh., "Role of silver ions in destabilization of intermolecular adhesion forces measured by atomic force microscopy in staphylococcus epidermidis biofilms". Antimicrobial Agents Chemotherapy 2005;49(12):4853-4859.
Otani Y, Tabata Y, Ikada Y., "Hemostatic capability of rapidly curable glues from gelatin, poly(L-glutamic acid) and carbodiimide". Biomaterials 1998;19(22):2091-2098.

* cited by examiner

*Primary Examiner* — Robert Landsman
(74) *Attorney, Agent, or Firm* — Bartony & Associates, LLC

(57) ABSTRACT

A composition includes at least one biologically active agent covalently attached to a first polymerizing molecule that is adapted to undergo a free radical polymerization. The first polymerizing molecule retains the ability to undergo free radical polymerization after attachment of the bioactive agent thereto. The first polymerizing molecule is preferably biocompatible. The polymerizing molecule can, for example. be dihydroxyphenyl-L-alanine (DOPA) or tyrosine. The composition can also include a second component synthesized by reacting at least one core molecule having a plurality of reactive hydrogen groups with at least one multi-isocyanate functional molecule to create a conjugate including terminal isocyanate groups. The conjugate molecule is reacted with a second polymerizing molecule that is adapted to undergo a free radical polymerization. The second polymerizing molecule includes a reactive hydrogen to react with the isocyanate groups of the conjugate. The second polymerizing molecule retains the ability to undergo the free radical polymerization after reaction with the conjugate. In several embodiments, the first polymerizing molecule and the second polymerizing molecule are the same and dihydroxyphenyl-L-alanine (DOPA) or tyrosine.

44 Claims, 24 Drawing Sheets

SG- PEG, LDI, DOPA, Collagen, Lidocaine, Ag, peroxydiphosphate)
LG- PEG, LDI, DOPA, Collagen, Lidocaine ated by the US Army
WOUND HEALING POLYMERIC NETWORKS

CROSS-REFERENCE TO RELATED APPLICATIONS

The present application claims benefit of U.S. Provisional Patent Application Ser. No. 60/695,912, filed Jul. 1, 2005, and U.S. Provisional Patent Application Ser. No. 60/789,372, filed Apr. 5, 2006, the disclosures of which are incorporated herein by reference.

GOVERNMENT INTERESTS

This invention was made with government support under grant #DAMD 17-02-1-0717 awarded by the US Army MRMC. The government has certain rights in this invention.

BACKGROUND OF THE INVENTION

The present invention relates generally to wound healing polymeric networks, matrices, or gels, to compositions and compounds to form wound healing polymeric networks, to methods of synthesizing wound healing polymeric networks and to methods of treating wounds using wound healing polymeric networks.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Wound healing is a dynamic and orchestrated process that involves cellular and matrix components acting together to re-establish the lost tissues. Co-morbid physiological and psychological conditions and aging compromise this healing, which can be ameliorated by modulating these underlying conditions (with the exception of aging). Infections adversely impact wound repair through ongoing chronic inflammation and production of toxic molecules and metabolites from both the microbe and the immune response. Skin wounds are particularly prone to these infections as they are both exposed to pathogens and also harbor commensural microbes that can infect compromised tissue. Thus microbial proliferation must be controlled or prevented to enable proper healing.

The existence of a variety of wound types with varied healing modes and phases has led to the development of different types of wound healing matrices in attempts to improve upon physiological healing. Traditional wound management involves disinfection and provision of a moist environment to encourage the establishment of the best environment for the natural healing process. The use of biological sealants has been promoted primarily based on their ability to enhance coagulation in addition to their capacity to create a mechanical barrier at the site of bleeding.

In designing a material or matrix to promote wound healing, one that is capable of providing adequate antimicrobial activity is desired provided that the antimicrobial substance(s) present in the matrix do not compromise the physiologic healing, including hemostasis and immune functioning and the repair-promoting physiochemical aspects of the matrix. To be beneficial, the antimicrobial agent preferably exerts its effect over the relevant time scale of days, without being washed out by tissue fluid flows or neutralized by serum- and tissue-derived factors and enzymatic activities.

With the surge of antibiotic resistance, impregnating a matrix with a necessarily broad-spectrum antibiotic is becoming a concern. Moreover, complex molecules may form complexes with the surface of polymer and modify it further resulting in confounding diffusion and elution calculations. This also may produce novel immunological epitopes that would be recognized by the body as foreign.

Silver is a widely used nonspecific antimicrobial, as it acts against a very broad spectrum of bacterial, yeast and fungal species likely to contaminate wounds and body cavities. See, for example, Thomas S, McCubbin P. A comparison of the antimicrobial effects of four silver-containing dressings on three organisms. J Wound Care 2003; 12(3):101-7. This action derives from the binding of the positive silver ions with the negatively charged microbial proteins preventing their replication, and via attachment to sulfhydryl groups, preventing their respiration and resulting in inhibiting their proliferation. See, for example, Holt K B, Bard A J. Interaction of silver(I) ions with the respiratory chain of *Escherichia coli*: an electrochemical and scanning electrochemical microscopy study of the antimicrobial mechanism of micromolar Ag+. Biochemistry 2005; 44(39):13214-23; Bragg P D, Rainnie D J. The effect of silver ions on the respiratory chain of *E. coli*. Can J Microbiol 1974; 20(6):883-9; and Darouiche R O. Anti-infective efficacy of silver-coated medical prostheses. Clin Infect Dis 1999; 29(6):1371-7. Silver also works on biofilms, a critical challenge for embedded foreign bodies. See, for example, Chaw K C, Manimaran M, Tay F E. Role of silver ions in destabilization of intermolecular adhesion forces measured by atomic force microscopy in staphylococcus epidermidis biofilms. Antimicrob Agents Chemother 2005; 49(12):4853-9.

Currently available products for facilitation of wound healing have met with only limited success. It thus remains desirable to develop wound healing polymeric networks, compounds for forming such wound healing polymeric networks, methods of synthesizing or forming such wound healing polymeric networks and methods of treating wounds using such wound healing polymeric networks.

SUMMARY OF THE INVENTION

In one aspect the present invention provides a composition including at least one biologically active agent covalently attached to a polymerizing molecule that is adapted to undergo a free radical polymerization. The polymerizing molecule retains the ability to undergo free radical polymerization after attachment of the bioactive agent thereto. The polymerizing molecule is preferably biocompatible. The polymerizing molecule can, for example, be dihydroxyphenyl-L-alanine (DOPA), a derivative of dihydroxyphenyl-L-alanine, histidine, a derivative of histidine, lysine, a derivative of lysine, tryptophan, a derivative of tryptophan, tyrosine or a derivative of tyrosine. In several embodiment, the polymerizing molecule is dihydroxyphenyl-L-alanine (DOPA) or tyrosine.

A functional group on the biologically active molecule can, for example, be reacted (either directly or indirectly) with a functional group on the polymerizing molecule. In several embodiments, the functional group on the polymerizing molecule is modified to make it reactive with the functional group on the biologically active agent. For example, in the case that the polymerizing molecule is dihydroxyphenyl-L-alanine, the dihydroxyphenyl-L-alanine can be reacted with N-hydroxysuccinimide to create an "active DOPA" which can, for example, react with amine groups of the biologically active agent (for example, a protein such as collagen). The secondary amine of dihydroxyphenyl-L-alanine can be protected before the reaction with N-hydroxysuccinimide.

In several embodiments, the composition further includes a second or synthetic component synthesized by reacting at least one core molecule having a plurality of reactive hydrogen groups with at least one multi-isocyanate functional molecule to create a conjugate including isocyanate groups. The conjugate molecule is reacted with a polymerizing molecule that is adapted to undergo a free radical polymerization. The polymerizing molecule includes a reactive hydrogen to react with the isocyanate groups of the conjugate. The polymerizing molecule retains the ability to undergo the free radical polymerization after reaction with the conjugate.

The core molecule can, for example, be one or more of glycerol, diglycerol, ascorbic acid, a saccharide, pentaerythritol, xylitol, arabitol, fucitol, ribitol, gluconic acid, glucosamine, sorbitol, mannitol, a steroid or a biocompatible multi-functional polymer. The multi-isocyanate functional molecule can, for example, be formed from a biocompatible multi-amine functional precursors. In several embodiments, the multi-isocyanate functional compounds is lysine di-isocyanate, a lysine di-isocyanate derivative, lysine tri-isocyanate, a derivative of lysine tri-isocyanate or putrescine. The polymerizing molecule can, for example, be dihydroxyphenyl-L-alanine (DOPA) a derivative of dihydroxyphenyl-L-alanine (DOPA), histidine, a derivative of histidine, lysine, a derivative of lysine, tryptophan, a derivative of tryptophan, tyrosine or a derivative of tyrosine. In several embodiment, the polymerizing molecule is dihydroxyphenyl-L-alanine (DOPA) or tyrosine and is the same as the polymerizing molecule covalently attached to the biologically active agent.

The composition can further include an initiating component adapted to initiate free radical polymerization. The initiating component can, for example, include silver or a silver compound (for example, a source of silver ions). The initiating component can further include peroxydiphosphate. In several embodiments, silver or a silver compound is present in a concentration suitable to initiate polymerization. The concentration is preferably below that substantially toxic to cells such as mammalian (for example, human) cells. Further, the concentration is preferably suitable such that the silver or silver compound functions as an antimicrobial agent. The silver or the silver compound can, for example, persist within a polymeric network formed from the composition in an antimicrobial level for at least one week in a wound. In several embodiments, the concentration of silver or of the silver compound is in the range of approximately 5 µg/ml to approximately 20 µg/ml based upon the volume of uncured (that is, unpolymerized) components of the composition.

Biologically active agents suitable for use in the present invention include, but are not limited to, at least one of a protein, an organic catalyst, a ribozyme, an organometallic, a glycoprotein, a glycosaminoglycan, a peptide, a polyamine, a polyamino acid, an antibody, a nucleic acid, a steroidal molecule, an antibiotic, an antiviral, an antimycotic, an anticancer agent, an analgesic agent, an antirejection agent, an immunosuppressant, a cytokine, a carbohydrate, an oleophobic, a lipid, extracellular matrix, an individual component of extracellular matrix, a growth factor, a hemostatic agent, a virus, a vireno, a virus vector or a prion.

In several embodiments, the biologically active agent includes extracellular matrix or a component of extracellular matrix. The biologically active agent can also include a hemostatic surface. For example, the biologically active agent can include collagen, fibrin or plasmin.

In several embodiments, the biologically active agent include a growth factor, including, for example, EGF, TGFa, PDGF, VEGF, IGF-1, FGF, HGF, KGF, TGFb, a CXCR3 ligand, IL-10 or IL-4.

The biologically active agent can include a hemostatic agent such as a small molecule hemostatic agent (for example, ATP, a derivative of ATP, epinephrine or a derivative of epinephrine).

In several embodiments, the biologically active agent includes an agent selected to promote at least one of cell adhesion, cell proliferation or cell migration. The biologically active agent can, for example, include sites for binding of at least one of beta1 or beta3 integrins.

The biologically active agent can also include an analgesic agent. The analgesic agent can, for example, be a topical anesthetic. The biologically active agent can also include an antimicrobial agent. The antimicrobial agent can, for example, be a macrolide, a topoisomerase inhibitors or a cephalosporin.

The compositions of the present invention can, for example, also include a free biologically active agent. As used herein, the term "free biologically active agent" refers to a biologically active agent that is not chemically bonded within the matrix created by the polymerized compositions of the present invention, but is, for example, physically entrapped therein or surrounded thereby. Such free biologically active agent can be release from the matrix over time.

In another aspect, the present invention provides a method of treating a wound including the steps of placing a composition in contact with the wound, wherein the composition includes at least one biologically active agent covalently attached to a polymerizing molecule that is adapted to undergo a free radical polymerization, the polymerizing molecule retaining the ability to undergo free radical polymerization after attachment of the bioactive agent thereto, and initiating polymerization.

In another aspect, the present invention provides a composition including a first component comprising at least one biologically active agent covalently attached to a first polymerizing molecule that is adapted to undergo a free radical polymerization. The first polymerizing molecule retains the ability to undergo free radical polymerization after attachment of the bioactive agent thereto. The composition also includes a second component synthesized by reacting at least one core molecule having a plurality of reactive hydrogen groups with at least one multi-isocyanate functional molecule to create a conjugate including terminal isocyanate groups. The conjugate molecule is reacted with a second polymerizing molecule that is adapted to undergo a free radical polymerization. The second polymerizing molecule includes a reactive hydrogen to react with the isocyanate groups of the conjugate. The second polymerizing molecule retains the ability to undergo the free radical polymerization after reaction with the conjugate. In several embodiments, the first polymerizing molecule and the second polymerizing molecule are the same and are dihydroxyphenyl-L-alanine (DOPA) or tyrosine.

The present invention, along with the attributes and attendant advantages thereof, will best be appreciated and understood in view of the following detailed description taken in conjunction with the accompanying drawings.

DETAILED DESCRIPTION OF THE INVENTION

Figure 1:
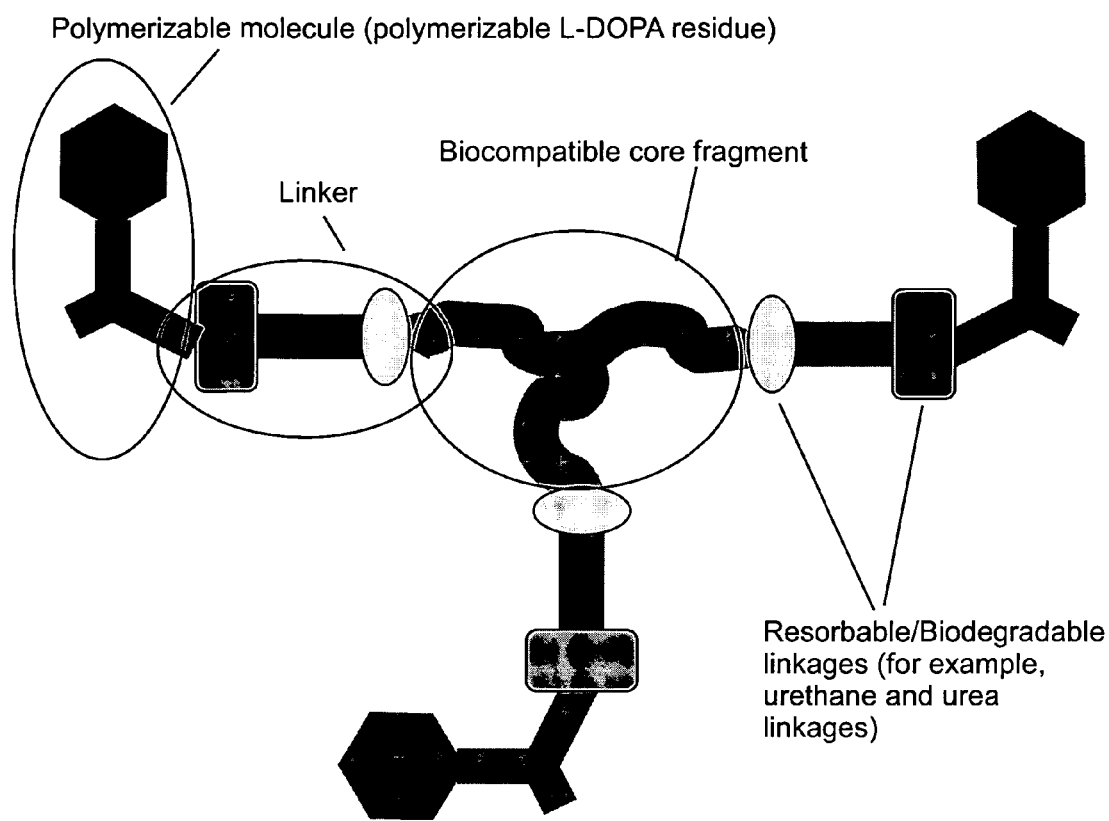
FIG. 1 illustrates a prepolymer of the present invention synthesized from a glycerol core molecule, a lysine diisocyanate linker molecule and L-DOPA.

A material for use as a wound healing matrix preferably exhibits, for example, several or more of the following desirable characteristics: the material is liquid prior to use or polymerization; solidifies in a controllable time frame when applied to wound; is nonirritating locally; is nontoxic systematically in the amount required to achieve an effective wound closure; exhibits hemostatic properties; alleviates pain; has appropriate flexibility (elastomeric); and/or is biodegradable so that the material does not disturb wound healing.

As used herein, the term "biodegradable" refers generally to the ability of the material to be broken down (especially into innocuous degradation products) over time in the environment of use (that is, within the body/wound). As used herein, the term "biocompatible" refers generally to compatibility with living tissue or a living system. In that regard, the precured liquid components, the polymer networks and the degradation products of the present invention are preferably biocompatible, substantially nontoxic and/or substantially non-injurious to the living tissue or living system in the amounts required over the period of contact/exposure. Moreover, such materials preferably do not cause a substantial immunological reaction or rejection in the amounts required over the period of contact/exposure. As used herein, the term "nontoxic" generally refers to substances which, upon ingestion, inhalation, or absorption through the skin by a human or animal, do not cause, either acutely or chronically, damage to living tissue, impairment of the central nervous system, severe illness or death. Preferably, the term "nontoxic" as used herein is understood in a relative sense and includes, for example, substances that have been approved by the United States Food and Drug Administration ("FDA") for administration to humans or, in keeping with established regulatory criteria and practice, are susceptible to approval by the FDA for administration to humans. In addition to FDA approval or approvability, nontoxicity of compounds suitable for use in the present invention can generally be evidenced by a high LD50 as determined in animal studies (for example, rat studies). Preferably, a nontoxic compound has an LD50 of over 1000 mg/kg; and, more preferably, has an LD50 of over 1500 mg/kg, and, even more preferably, has an LD50 of over 2000 mg/kg.

With the above considerations, we have developed wound healing matrices which are space-forming, biocompatible and degradable over, for example, a two to three week-long period. The terms polymeric network, matrix and gel are used interchangeably herein and refer to a polymer system (for example, a crosslinked polymeric network). These polymers were produced in a two part synthetic scheme with gelation preferably being catalyzed by ionic silver (Ag) with peroxydiphosphate. This mode of catalysis is preferred as silver, which distributes through the matrix passively, is widely used as an antimicrobial. In that regard, the self-curing polymers of the present invention could represent foreign bodies, which may form nidi for infection. Further, the distribution of silver through the polymer matrix operates to limit the growth of bacteria and yeast that commonly infect skin wounds, delaying the healing process. The wound healing matrices of the present invention are biocompatible to living tissues and exhibit hemostatic properties.

In several embodiments, crosslinked polymer networks, matrices or gels of the present invention were formed from a "synthetic component" comprising a prepolymer component formed from one or more multi-functional core molecules. Functional groups of the core molecule(s) are reacted with a first functional group of one or more multifunctional linker or spacer molecules. A second functional group of the linker molecule is reacted with a functional group of one or more molecules that can undergo a polymerization (for example, a free radical polymerization) under relatively benign condition. Preferably, the linker molecule is chosen so that biodegradable covalent bonds are formed between the linker molecule and the core molecule and between the linker molecule and the polymerizing molecule. The degradation products (generally, the core molecule or a derivative thereof, the linker molecule or a derivative thereof and the polymerizing molecule or a derivative thereof) are biocompatible.

The polymerizing molecule must retain the ability to polymerize after reaction with the linker molecule. In general, the polymerizing molecules of the present invention include one or more functional groups suitable to undergo a free radical polymerization as described herein (for example, a hydroxyphenyl group as present in DOPA and tyrosine). The polymerizing molecules also includes one or more functional groups suitable to effect covalent attachment (either directly or indirectly through one or more chemical moieties) of, for example, a linker molecule thereto or covalent attachment of a biologically active components thereto.

In several embodiments of the present invention, one or more multi-isocyanate functional molecules derived from one or more biocompatible multi-amine functional precursors was used as the linker molecule(s). Aliphatic multi-isocyanate functional molecules are preferred. In several embodiments of the present invention, the multi-amine functional precursor compounds of the multi-isocyanate functional compounds are biocompatible amino acids or biocompatible derivatives of an amino acids. For example, the multi-amine functional precursor compound can be lysine. The multi-isocyanate functional compounds can, for example, include lysine di-isocyanate or lysine di-isocyanate derivatives (for example, an alkyl ester of lysine-diisocyanate such as the methyl ester or the ethyl ester). The multi-isocyanate functional compounds can also include lysine tri-isocyanate or a derivative of lysine tri-isocyanate. Certain dipeptides (two amino acids linked by an amide linkage) can also be used. For example, lysine can be combined in a dipeptide with another amino acid (for example, lysine-valine, lysine glysine etc.). Another example of a multi-amine functional compound suitable for use in the present invention is putrescine (diamino butane). In several representative studies of the present invention lysine diisocyanate was used as the linker molecule.

In the case that one or more multi-isocyanate compounds are used as the linker molecule(s), the core molecule(s) should include reactive hydrogen functional groups (for example, hydroxy groups, primary amine groups, secondary amine groups or thiol groups). Once again, the core molecule is preferably biocompatible. Examples of suitable core molecules include, but are not limited to, glycerol, diglycerol, ascorbic acid, a saccharide (for example. glucose, lactose etc.), pentaerythritol, xylitol, arabitol, fucitol, ribitol, gluconic acid, glucosamine, sorbitol, mannitol, sugar alcohols generally, a steroid and biocompatible multi-functional polymers (for example, multi-hydroxy functional polyethylene glycol or PEG, a polyamino acid, a polyether or a polyester). Preferably, the core molecule, the linker molecule and the polymerizing molecule are selected so that the synthetic components is liquid or flowable prior to curing/polymerization.

In a number of studies of the present invention, polyethylene glycol, glycerol, ascorbic acid, glucose, and lactose were used as core molecules. The functionality of the core material determines the functionality of the resulting network after curing as illustrated, for example, in FIG. 1, which illustrates a DOPA-containing prepolymer (DLG) formed from a trifunctional glycerol core molecule. In general, the core molecule was reacted with at least a stoichiometric amount (NCO:OH=2:1), and preferably with an excess of lysine diisocyanate, capping the reactive hydrogen groups (hydroxyl groups, in the studied examples), creating in the process a resorbable/degradable urethane link, and terminating the arms of the core with a reactive isocyanate group. The core-lysine conjugate is reacted with, for example, a polymerizable molecule such as L-DOPA, creating a multi-functional, DOPA-terminated precursor. Dialysis was used to purify the product. Each of the synthetic component precursors has the general formula Core-(Lys-DOPA)$_x$, wherein x is the functionality of the core molecule.

In general, other (preferably, biocompatible) compounds such as amino acids (including, but not limited to, histidine, lysine, tryptophan, and tyrosine) that can form crosslinks via free-radical chemistry, can be substituted for or potentially used in connection with L-DOPA.

Figure 2:
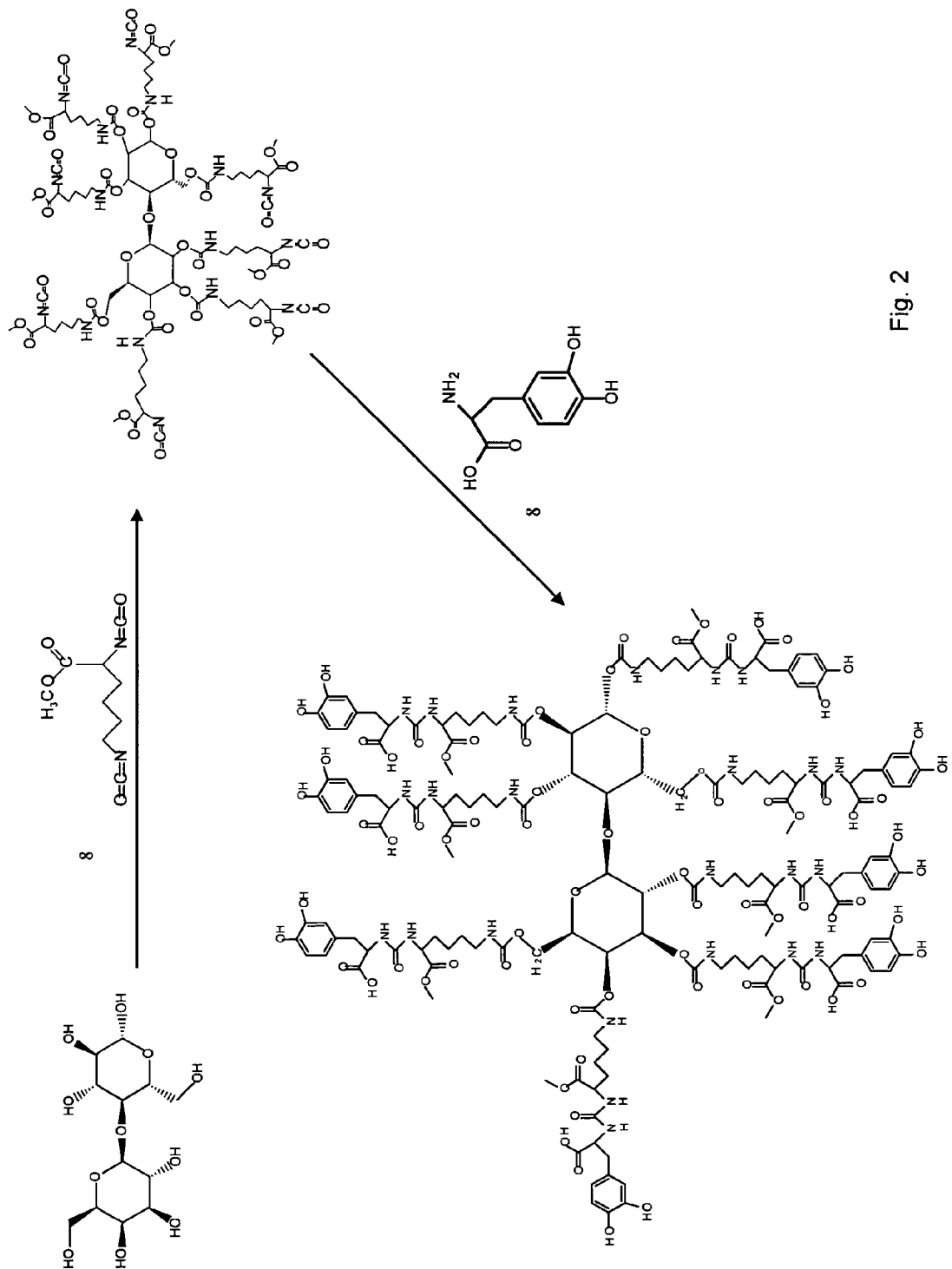
FIG. 2 illustrates a two-step reaction of the present invention for the synthesis of DOPA-containing prepolymer synthesized from a lactose core molecule.

A two step reaction scheme for synthesis of representative DOPA-containing prepolymers of the present invention is illustrated, for example, in FIG. 2 for a DOPA-containing prepolymer (DLL) formed from lactose. As described above in connection with a glycerol core molecule, in the first step, the hydroxyl groups from lactose were capped using LDI (molecular ratio was LDI:lactose=8:1; —NCO/—OH=2:1) to produce an isocyanate-terminated prepolymer. Upon 50% consumption of the isocyanate groups, as determined using FT-IR spectroscopy (using the height of the isocyanate peak at 2259 cm$^{-1}$ as a guide), the second reaction step was started by the addition of L-DOPA. In general, the same process was used for synthesis of DLG and a DOPA-containing prepolymer (DLP) formed using di-hydroxy functional PEG as the core molecule. Prepolymer synthesis was confirmed by the appearance of a strong absorption band at approximately 1714 cm$^{-1}$, in the IR, attributable to the formation of the urethane linkage (—NHCOO—), with the accompanying complete disappearance of the isocyanate group (—N=C=O; peak at 2259 cm$^{-1}$). $^1$H NMR spectrum of the product at first step, Lactose-(LDI)$_8$, showed that all hydroxyl groups of lactose has reacted with LDI (δ1.39, 16H; δ1.64, 16H; δ1.75, 16H; δ3.07, 8H; δ3.41, 24H; δ3.71, 16H; δ3.80, 1H; δ4.11, 4H; δ4.21, 8 H; δ4.54, 5H; δ6.05, 2H; δ6.25, 1H; δ6.54, 1H; δ7.75, 8H). The reaction mixture obtained by this two step synthesis was dialyzed and dried. $^1$H NMR spectrum of the final product, Lactose-(LDI-DOPA)$_8$ showed that DOPA has combined with the pre-polymer (δ1.22, 16H; δ1.30, 16H; δ1.50, 16H; δ2.96, 16H; δ3.28, 16H; δ3.46, 24H; δ3.52, 1H; δ3.91, 4H; δ4.01, 8H; δ4.10, 3H; δ4.21, 8H; δ5.68, 6H; δ5.71, 2H; δ5.80, 1H; δ6.10, 16H; δ6.32, 8 H; δ6.50, 16H; δ6.70, 1H; δ7.60, 8H; δ8.66, 8H). Similar results were observed in PEG-(LDI-DOPA)$_2$ and Glycerol-(LDI-DOPA)$_3$. Mass spectrum of PEG-(LDI-DOPA)$_2$ showed major fragment of [M$_{PEG}$+H+Na]$^{2+}$ at m/z=437.2, fragment of [M$_{DOPA}$+H]$^+$ at m/z=198.1, fragment of [M$_{DLP}$] at m/z=1232.6, fragment of [MDLP+4H]$^{4+}$ at m/z=1236.4, fragment of [M$_{DLP}$+H–M$_{DOPA}$+H$_2$O]$^+$ at m/z=1054.5. The fragments observed at m/z=840.2 and m/z=645.4 revealed the presence of [M$_{DLP}$–2M$_{DOP}$A+2H]$^{2+}$ and [M$_{PEG}$+LDI+H+H$_2$O]$^+$ Although the synthesis of the prepolymer using this methodology can be relatively slow, enhancement of the rate via the addition of a typical catalyst (dibutyl tin dilaurate, for example) would introduce potential downstream problems as a result of tin contamination. Further, any residual free isocyanate following completion of the reaction was hydrolyzed to amine during the extensive dialysis.

The synthetic component precursors of the present invention provide very desirable physiochemical properties for use in a wound healing matrix in that they are liquid prior to use/polymerization and solidify in a controllable time frame upon application to a wound. Moreover, the networks, matrices or gels formed therefrom are nontoxic and biocompatible (locally and systemically). Further, the gels degrade into the biocompatible building blocks thereof (for example, the core molecule(s), lysine (the multi-amino functional precursor of the multi-isocyanate) and DOPA) in a desirable period of time. However, as described further below, wound healing matrices formed solely from synthetic component precursors of the present invention can exhibit certain characteristics that can inhibit healing. For example, cell proliferation can be inhibited by such wound healing matrices. The present inventors have discovered that hybrid wound healing matrices formed, for example, from the synthetic component precursors of the present invention and a biological component that comprises a biologically active agent covalently attached to a polymerizing molecule (for example, that is adapted to undergo a free radical polymerization and retains the ability to undergo free radical polymerization after attachment of the bioactive agent thereto) provide good wound healing matrices.

Certain physiochemical characteristics of the wound healing matrices (for example, precure (liquid gel) viscosity, stiffness (or, conversely, elasticity), cure time, degradation time and rate of diffusion of certain elements from the wound healing matrices of the present invention can be controlled by appropriate design of the synthetic components of the wound healing matrices of the present invention. For example, increasing functionality of the core molecules (for example, as defined by decreasing equivalent weight thereof—molecular weight divided by functionality) results in an increase in precure viscosity, an increase in stiffness of the resulting gel, a decrease in cure time, an increase in degradation time and a decrease in rate of diffusion of certain components (for example, silver) from the resulting gel.

A number of aspects of the present invention are illustrated through the discussion of a number of representative wound healing matrices of the present invention. For example, matrices formed from synthetic component precursors synthesized from lysine, DOPA and the core molecules glycerol, lactose and PEG are characterized. Further, the effects of incorporating one or more biological components such as extra cellular matrix or individual components thereof (for example, collagen) into the wound healing matrices of the present invention are illustrated.

Figure 3A:
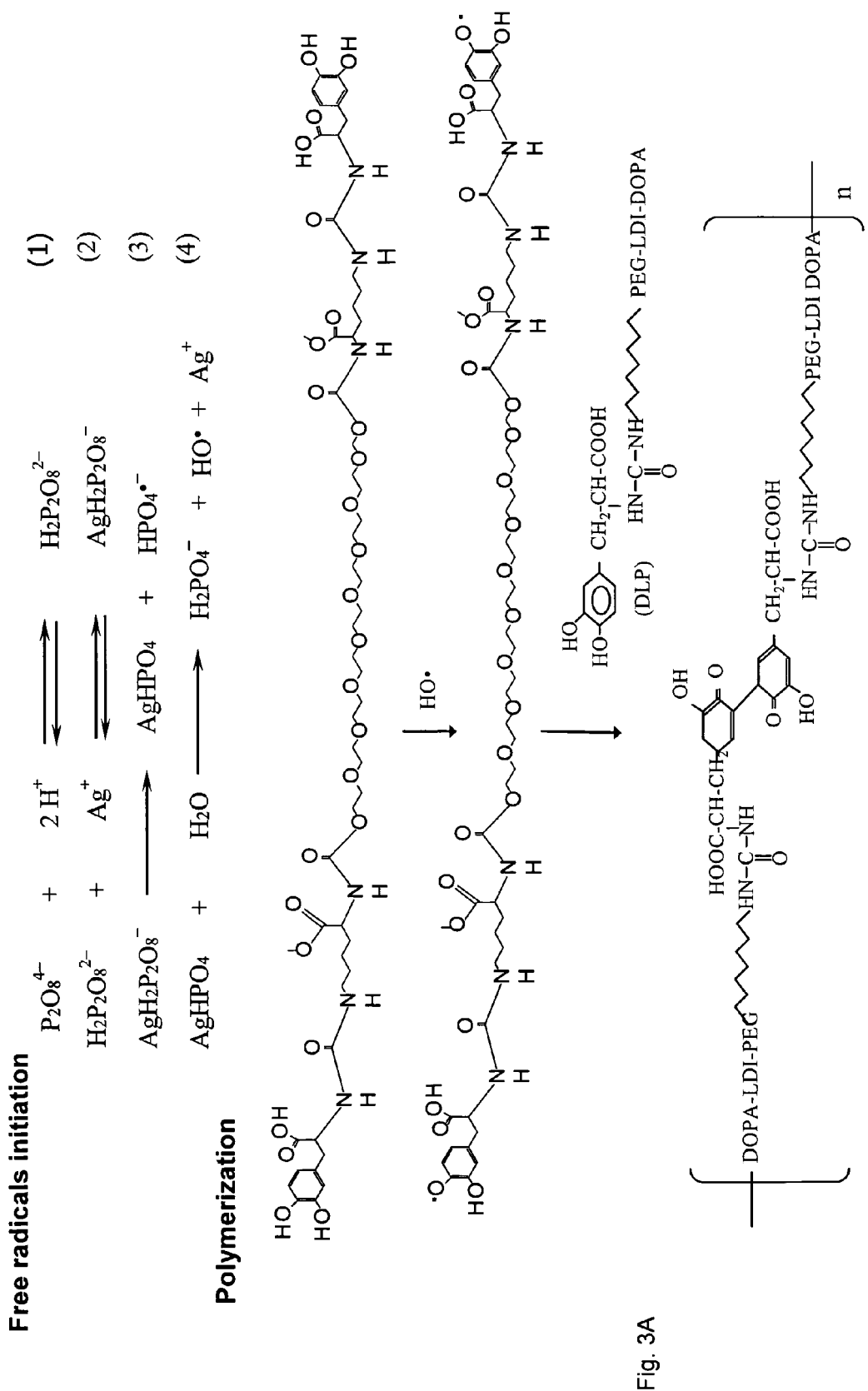
FIG. 3A illustrates cross-linking pathways for the DOPA-containing compounds of the present invention.
Figure 3B:
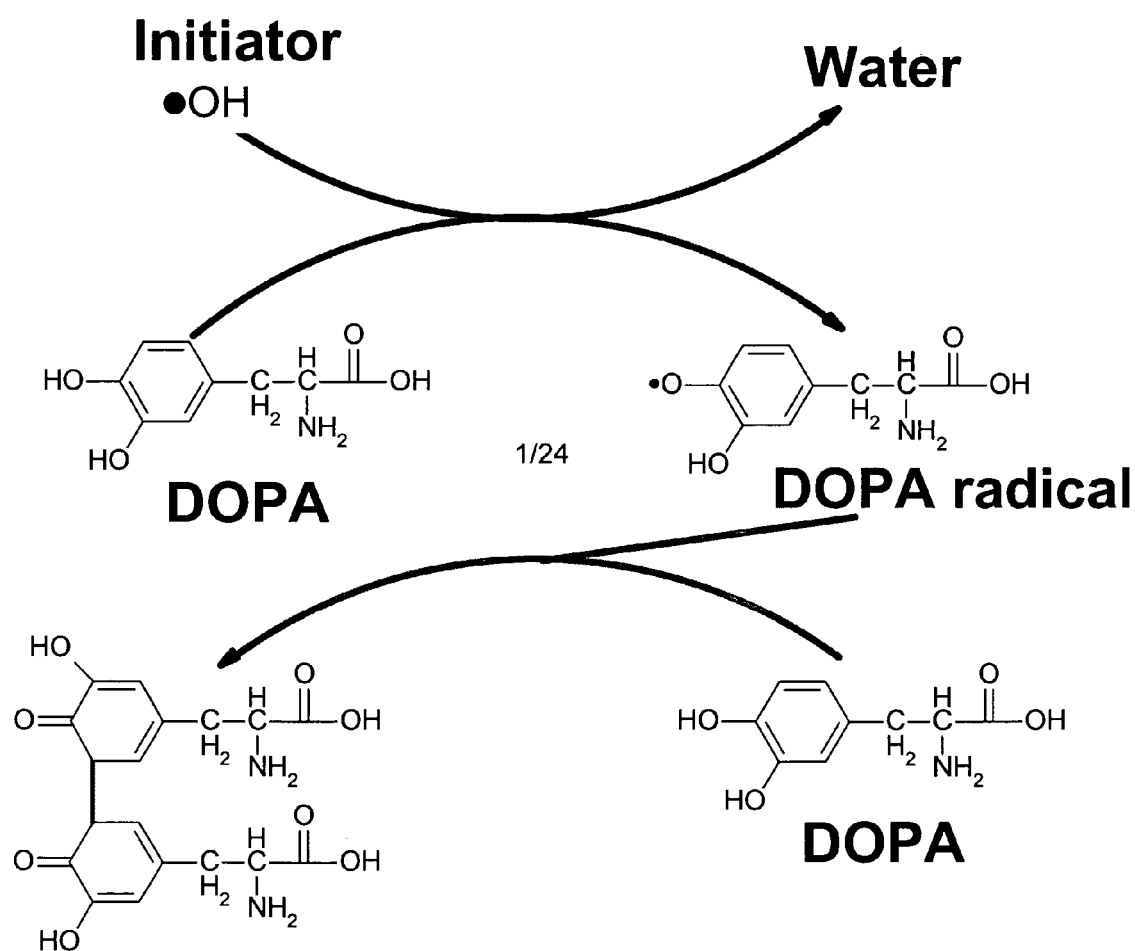
FIG. 3B further illustrates cross-linking pathways for the DOPA-containing compounds of the present invention.
Figure 4A:
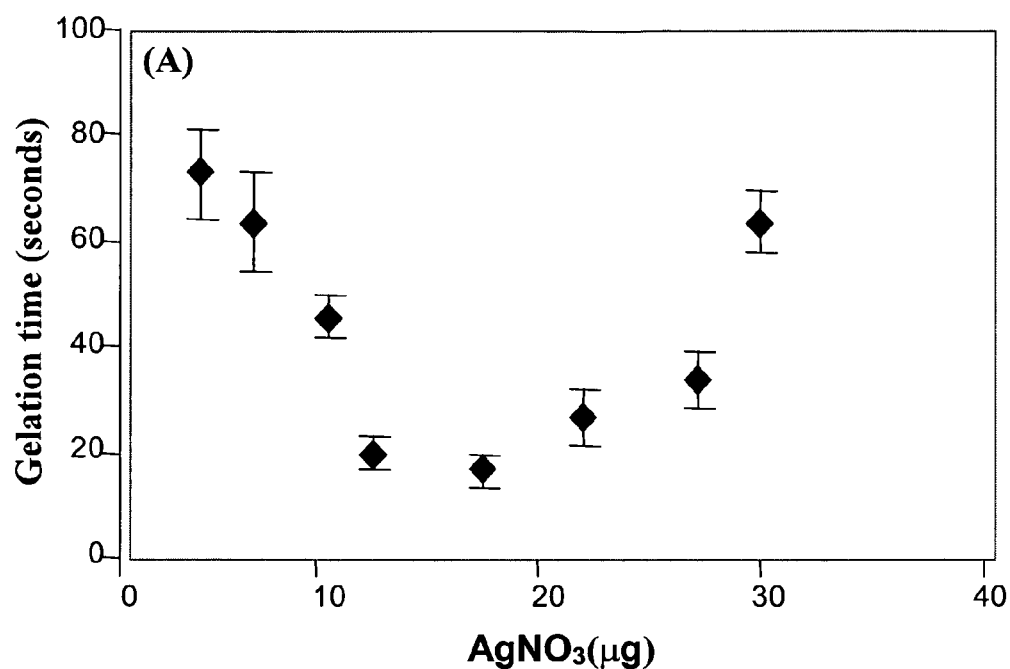
FIG. 4A illustrates the effect of the concentrations of silver nitrate on the polymerization of the DOPA-containing polymer wherein various concentrations of silver nitrate were added in 1 ml of DLL (0.3 g/ml, 300 mg) with 15 µg potassium peroxydiphosphate
Figure 4B:
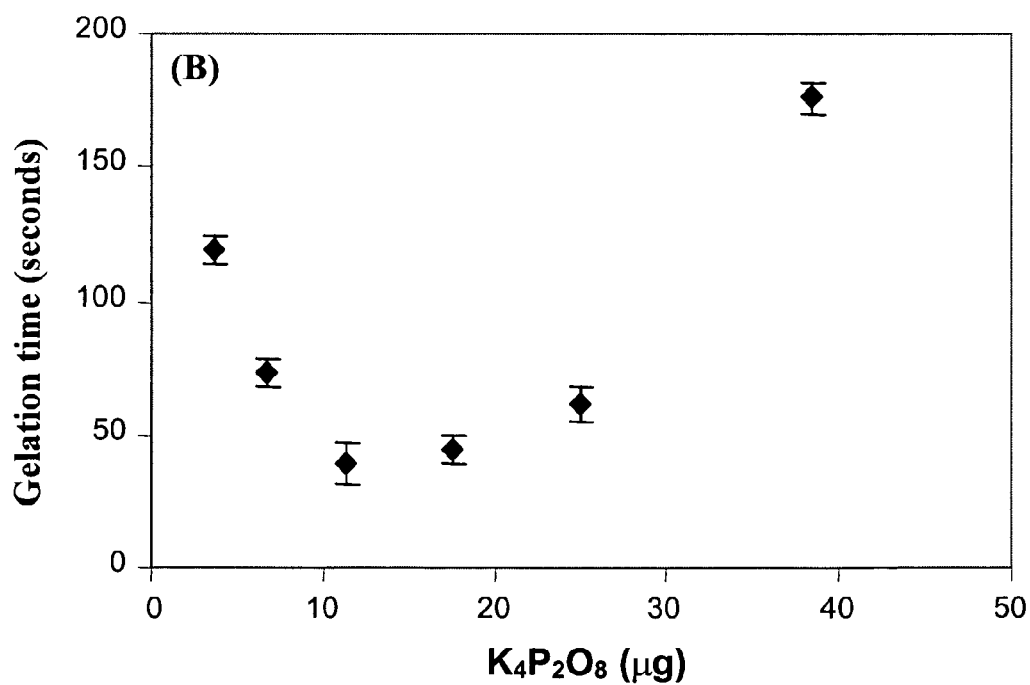
FIG. 4B illustrates the effect of the concentrations of potassium peroxydiphosphate on the polymerization of the DOPA-containing polymer. wherein various concentrations of peroxydiphosphate were added in 1 ml of DLL (0.3 g/ml, 300 mg) with 10 µg silver nitrate and each point was obtained by recording the curing time once potassium peroxydiphosphate was added.

One goal in designing the wound healing matrices of the present invention was to generate a polymer using molecules that could double as functional components of the matrix. Gupta has previously reported that an efficient redox initiating system for rapid free radical polymerization at mild temperatures was formed from $Ag^+$ and acid peroxydiphosphate in aqueous media. Gupta K C. Kinetics of radical polymerization of N-vinylpyrrolidone by peroxydiphosphate-Ag+ system. Appl Polym Sci 1994; 53:71-78. This redox initiation system is attractive as silver is used widely as an antimicrobial agent. In reacting DOPA with the core molecule-LDI conjugate to form the prepolymer, unprotected DOPA was used as the rate of reaction of the catechol side chain of DOPA is much slower than the rate or reaction of the amine group. Silver nitrate and potassium peroxydiphosphate were used as a redox couple to initiate polymerization of the prepolymers in the studies of the present invention. Without limitation to any mechanism, cross-linking pathways for the DOPA-containing compounds are illustrated in FIGS. 3A and 3B. To investigate the effect of the initiators on the polymerization, various concentrations of silver nitrate and potassium peroxydiphosphate (in 10 µl aliquots) were added to 1 ml of the DLL pre-polymer solution. As illustrated in FIGS. 4A and 4B, curing time exhibited a minimum as both the amount of silver and the amount of peroxydiphosphate were increased. At optimal levels of both peroxydiphosphate and silver, the cure time of the DLL pre-polymer could be reduced to approximately 10 seconds.

Figure 4C:
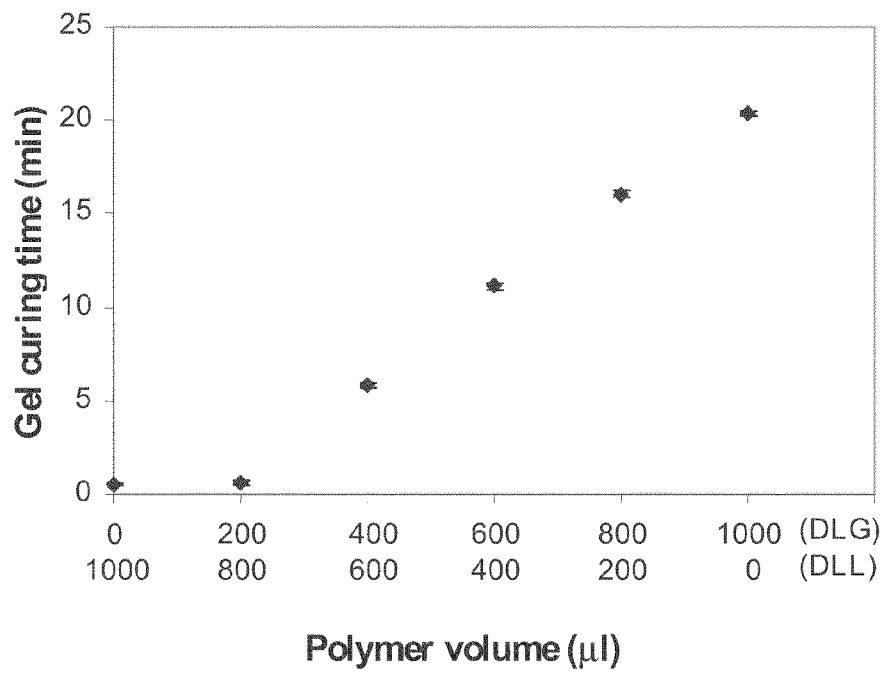
FIG. 4C illustrates the effect of the polymer structures on the gel curing time wherein 10 µg silver nitrate and 15 µg potassium peroxydiphosphate were added into each sample containing various amounts of DLL and DLG and the curing time recorded.
Figure 4D:
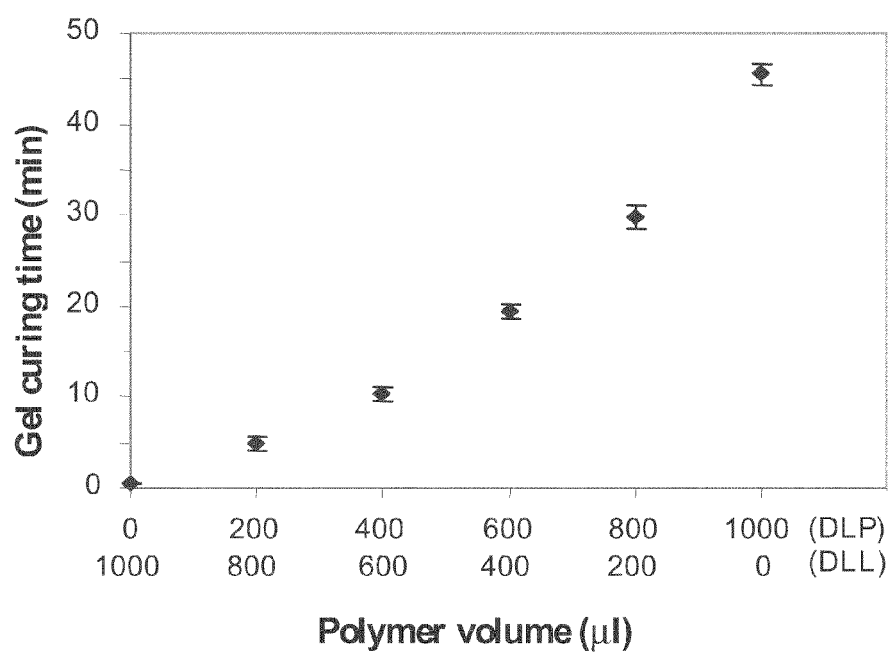
FIG. 4D illustrates the effect of the polymer structures on the gel curing time wherein 10 µg silver nitrate and 15 µg potassium peroxydiphosphate were added into each sample containing various amounts of DLL and DLP and the curing time recorded.

The structure of the pre-polymer also affected the cure time. As can be seen in FIGS. 4C and 4D, when mixtures of DLL (lactose-based), DLG (glycerol-based), and DLP (PEG-based) pre-polymer were employed, cure time increased as the average functionality of the mixture decreased.

Figure 5A:
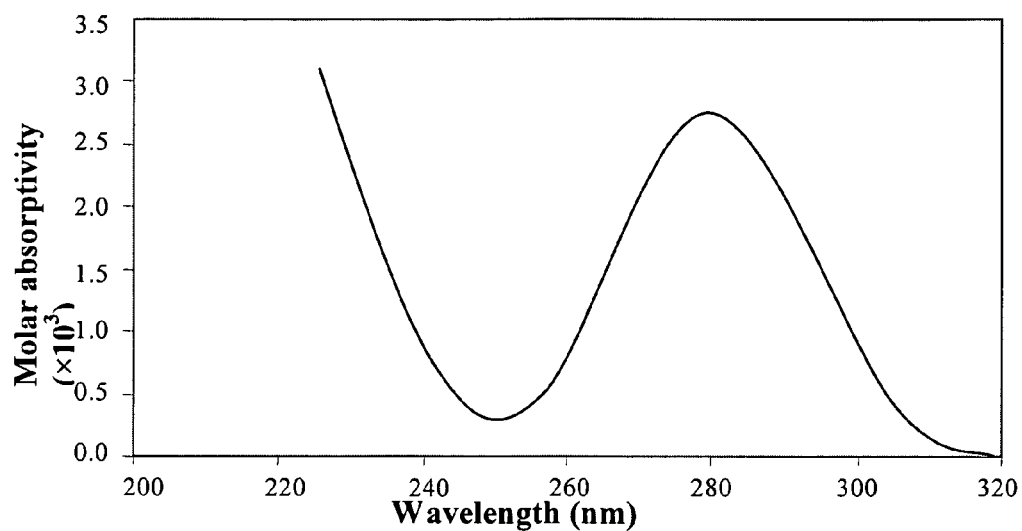
FIG. 5A illustrates a UV spectrum of DOPA with maximal absorbance in aqueous solution at 280 nm.
Figure 5B:
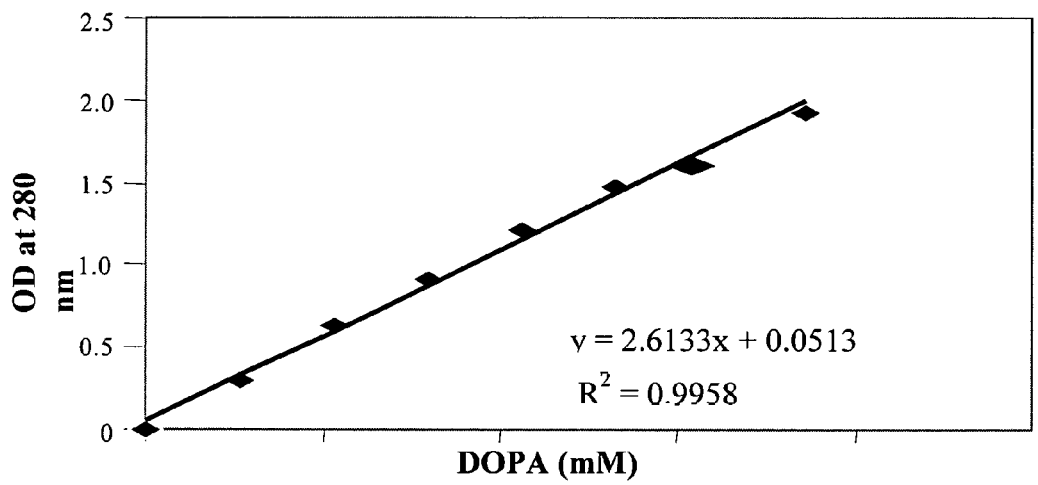
FIG. 5B illustrates a standard curve for DOPA which was obtained by the determination of OD at 280 nm and the correlation coefficient of the standard curve was 0.9958.

To be applicable as a wound healing matrix, the cured polymer preferably remains intact over a number of days. Polymer degradation was tested in vitro by placing 100 mg of polymer into 1 ml of phosphate buffer solution at 37° C. and changing the buffer daily. The rate of degradation was monitored by measuring the amount of DOPA released from the polymer gel as a function of time. As a 1,2-benzenediol, DOPA exhibits a maximum UV absorbance in aqueous solution at approximately 280 nm (see FIG. 5A). Since lysine, and core molecules such as lactose and PEG do not absorb significantly at this wavelength, the concentration of DOPA was determined by UV absorbance at 280 nm. The standard curve of DOPA is shown in FIG. 5B.

Figure 5C:
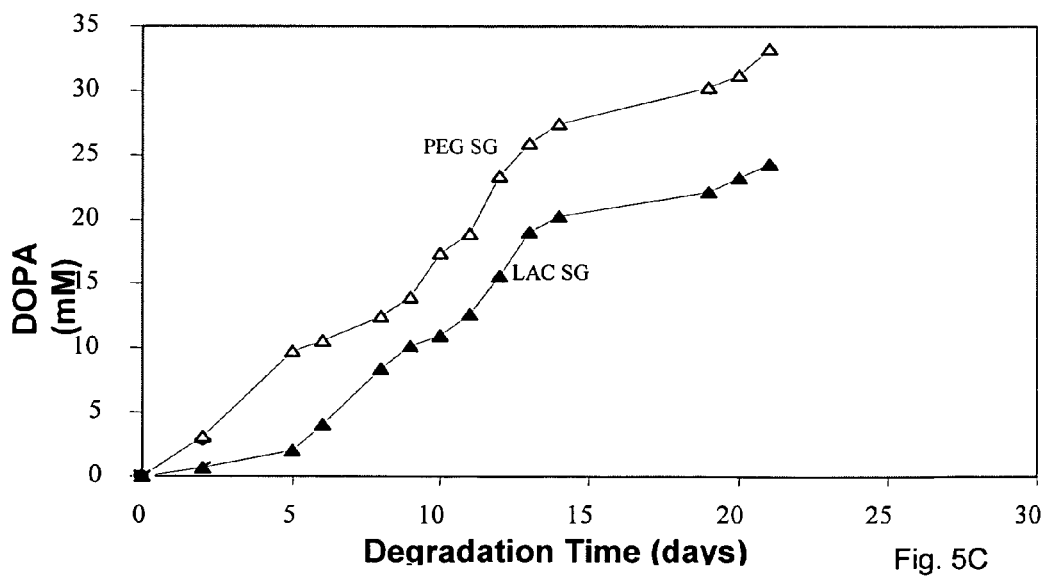
FIG. 5C illustrates the degradation of various DOPA-containing polymer gels in PBS wherein the polymer gels were incubated in PBS for three weeks and the degradation was tested by the concentration of DOPA released from the polymer gel into the solution (PEG SG-solid gel with PEG, LDI, DOPA, Ag and peroxydiphosphate; LAC LG-liquid gel with Lactose, LDI, DOPA, Ag and peroxydiphosphate).

Degradation testing indicated that the DOPA-containing polymers of the present invention were degraded over a period of approximately three weeks. Further, as shown in FIG. 5C using gels formed from mixtures of lactose and polyethylene glycol based prepolymers, the time required to achieve a certain extent of degradation increased as the functionality of the network increased. We measured the pH of the PBS containing 100 mg/ml polymer over a period of 21 days, the degradation products of the DOPA-containing polymers (PEG gel and Lactose gel) had no significant effect on the pH of polymer degradation solution at physiological temperature tested. These data indicate that a functional polymer can be generated from these materials.

Figure 6A:
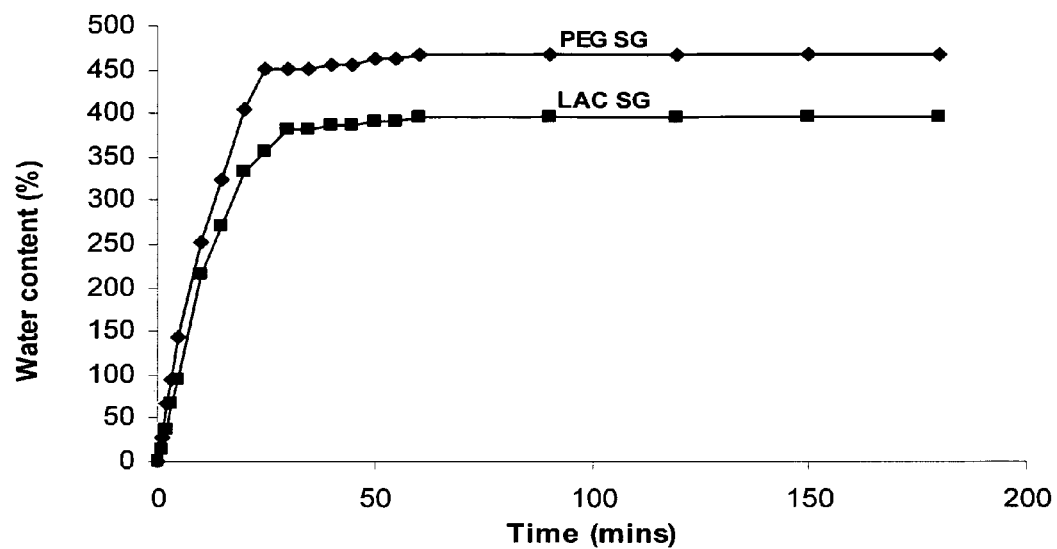
FIG. 6A illustrates swelling properties of the DOPA-containing gels of the present invention as a function of time at 37° C.
Figure 6B:
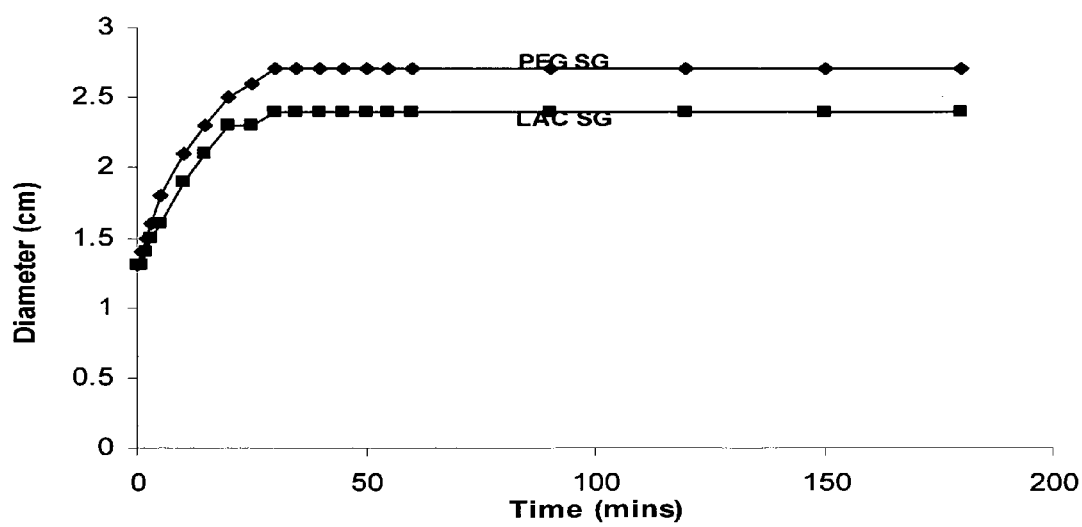
FIG. 6B illustrates the change in diameter of the DOPA-containing gels of the present invention as a function of time at 37° C. (PEG SG-PEG, LDI, DOPA, Ag, peroxydiphosphate; LAC SG-Lactose, LDI, DOPA, Ag, peroxydiphosphate)

Polymer gels of the present invention such as PEG or lactose containing polymer gels exhibited hydrophilic characteristics. As a consequence, the gels were observed to swell when placed in phosphate buffer solution at 37° C. As seen in FIG. 6A, the amount of uptake of water increased for the initial 30 minutes after which it attained its saturation point. This result was, to a degree, reflective of drug release capabilities of a wound matrix. In FIG. 6B, the change in diameter was also recorded to better understand the flexible nature of the polymer gels to its maximum extent. PEG gel exhibited a more hydrophilic character than Lactose gel.

Figure 7A:
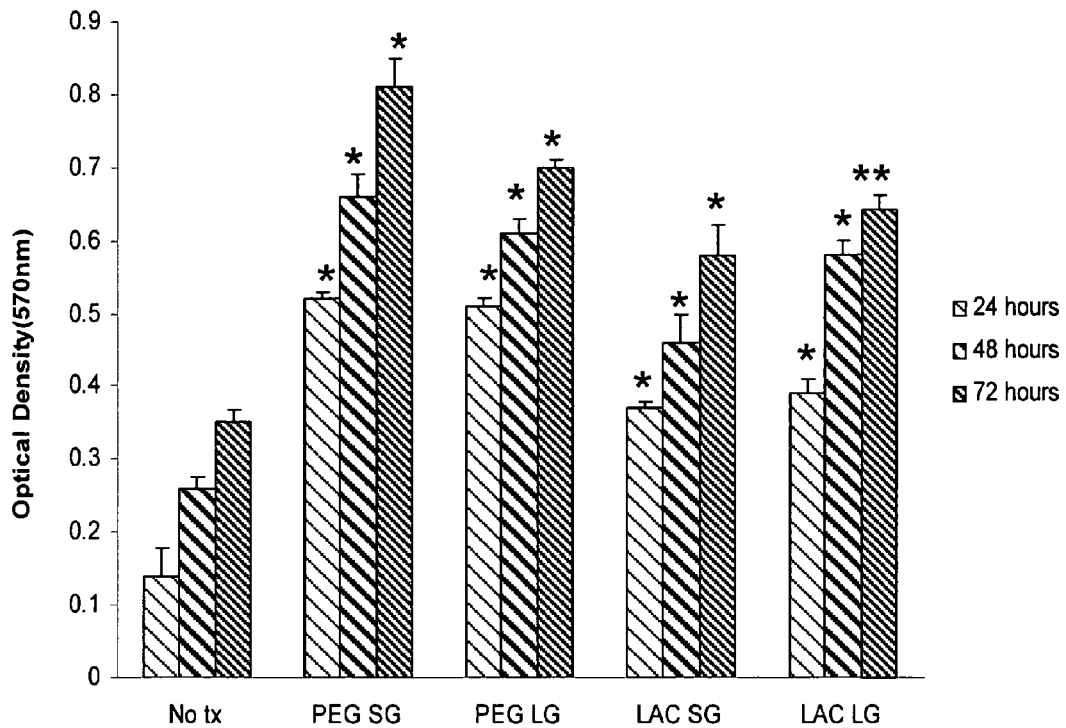
FIG. 7A illustrates the effect of DOPA-containing gels of the present invention on human dermal fibroblasts cell viability.
Figure 7B:
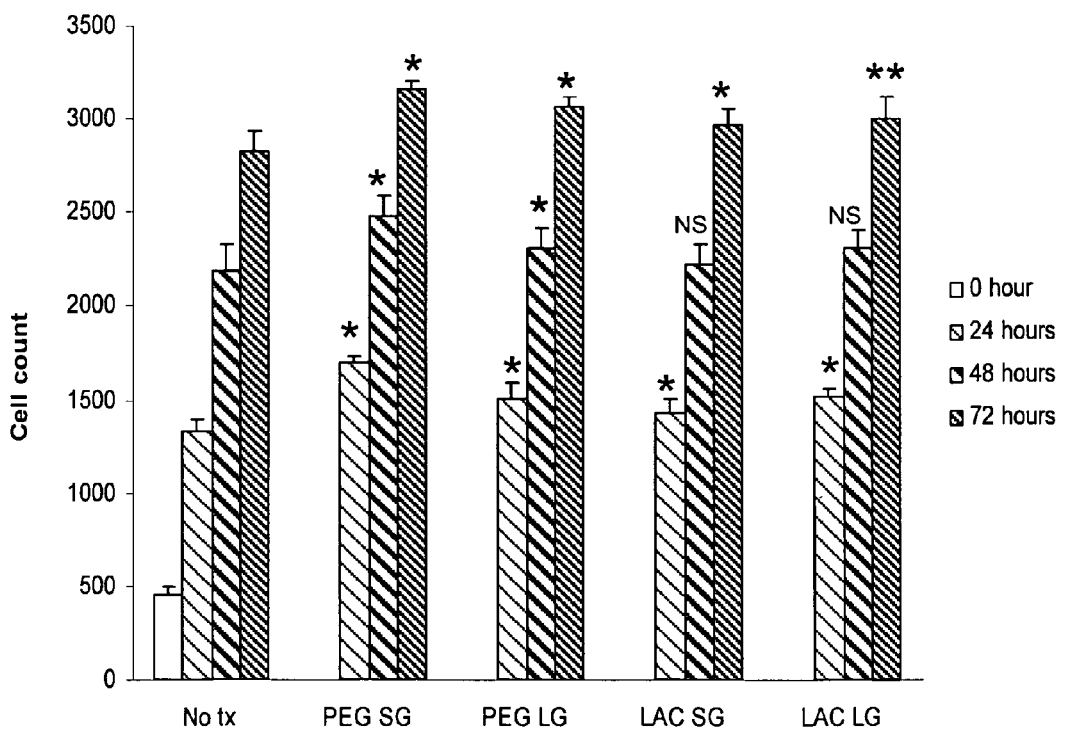
FIG. 7B illustrates the effect of DOPA-containing gels of the present invention on human dermal fibroblast cell proliferation wherein (in the studies of FIGS. 7A and 7B) cells were exposed to gels (PEG SG-solid gel with PEG, LDI, DOPA, Ag, and peroxydiphosphate; PEG LG-Liquid gel with PEG, LDI, and DOPA; LAC SG-solid gel with lactose, LDI, DOPA, Ag, and peroxydiphosphate; LAC LG-Liquid gel with lactose, LDI, and DOPA) after 48 hours in serum depleted media, wherein cell viability and proliferation were assessed at 24, 48 and 72 hours, and values are expressed as mean+/−SEM. (n=3) NS=Not significant, *=p<0.05, **=p<0.01 compared to diluent alone (No tx-No treatment).
Figure 8A:
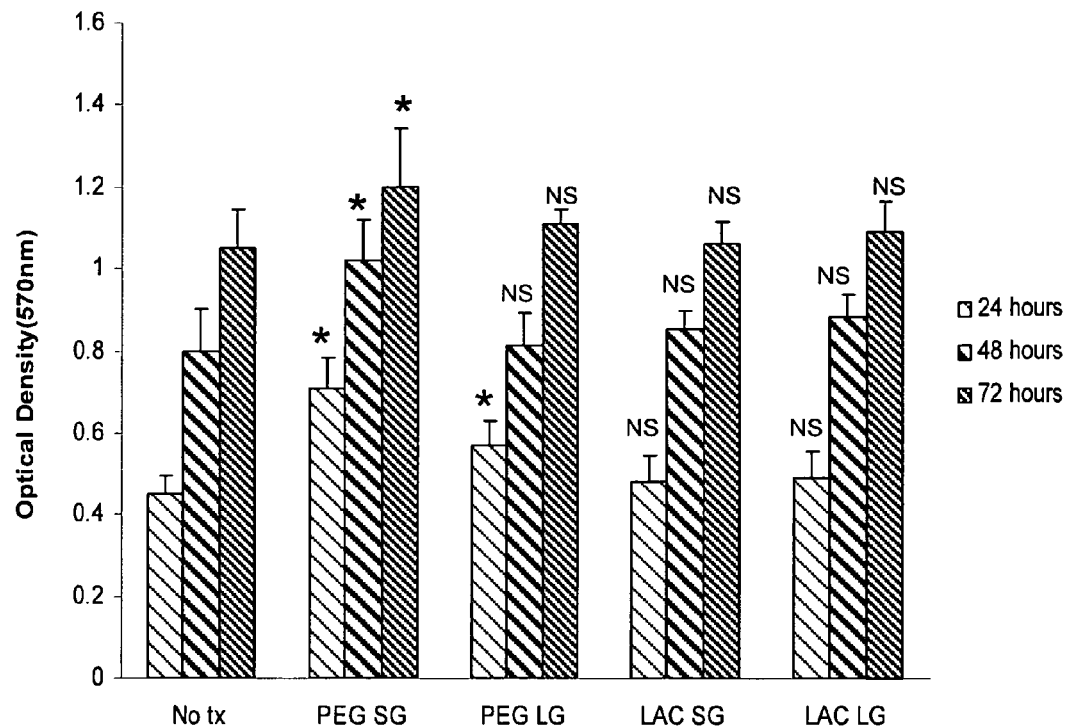
FIG. 8A illustrates the effect of DOPA-containing gels of the present invention on human keratinocytes cell viability.
Figure 8B:
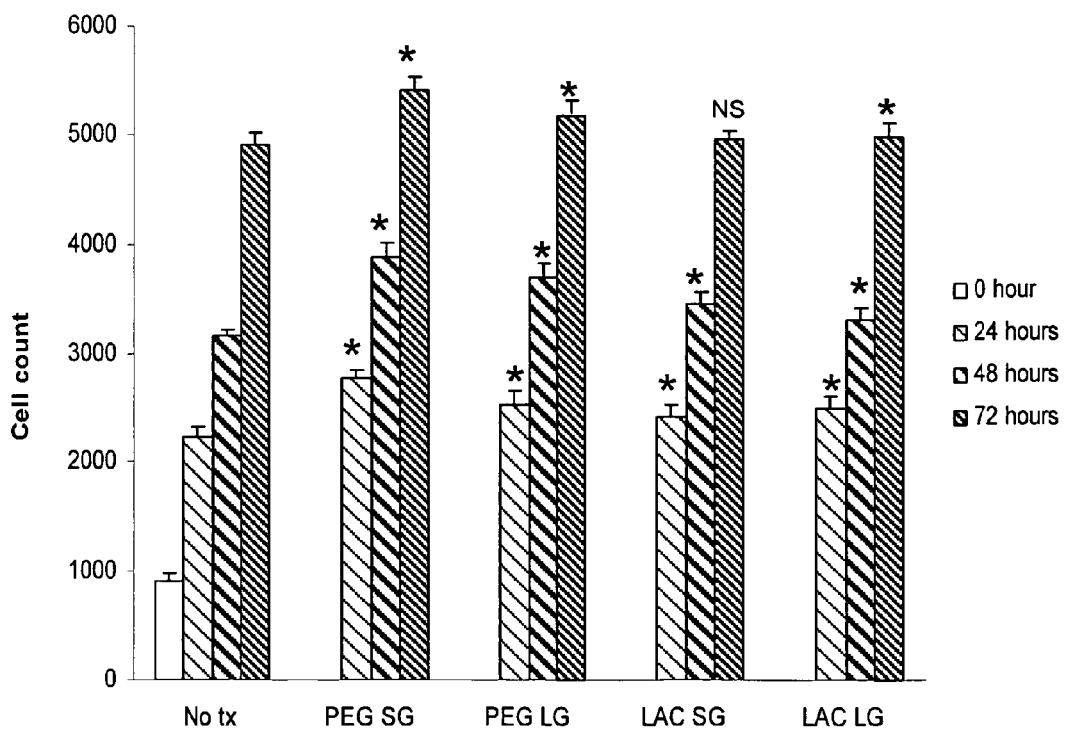
FIG. 8B illustrates the effect of DOPA-containing gels of the present invention on human keratinocytes cell proliferation, wherein (in the studies of FIGS. 8A and 8B) cells were exposed to gels with composition as described in connection with FIGS. 7A and 7B after 48 hours in serum depleted media, wherein cell viability and proliferation were assessed at 24, 48 and 72 hours, and values are expressed as mean+/−SEM. (n=3) NS=not significant, *=p<0.05 compared to diluent alone (No tx).

As the polymeric networks, matrices or gels of the present invention are to be placed in direct contact with the structural cells of skin, fibroblasts and keratinocytes, they are preferably nontoxic to such cells. Despite the Ag being broadly microbicidal, these gels did not compromise either the viability or growth of the fibroblasts (see FIGS. 7A and 7B) or keratinocytes (see FIGS. 8A and 8B). This result was observed both for gelated polymers (SG, solid gel) and uncured components thereof (in which the catalysts were omitted, which are sometimes referred to herein as LG or liquid gels).

Figure 9A:
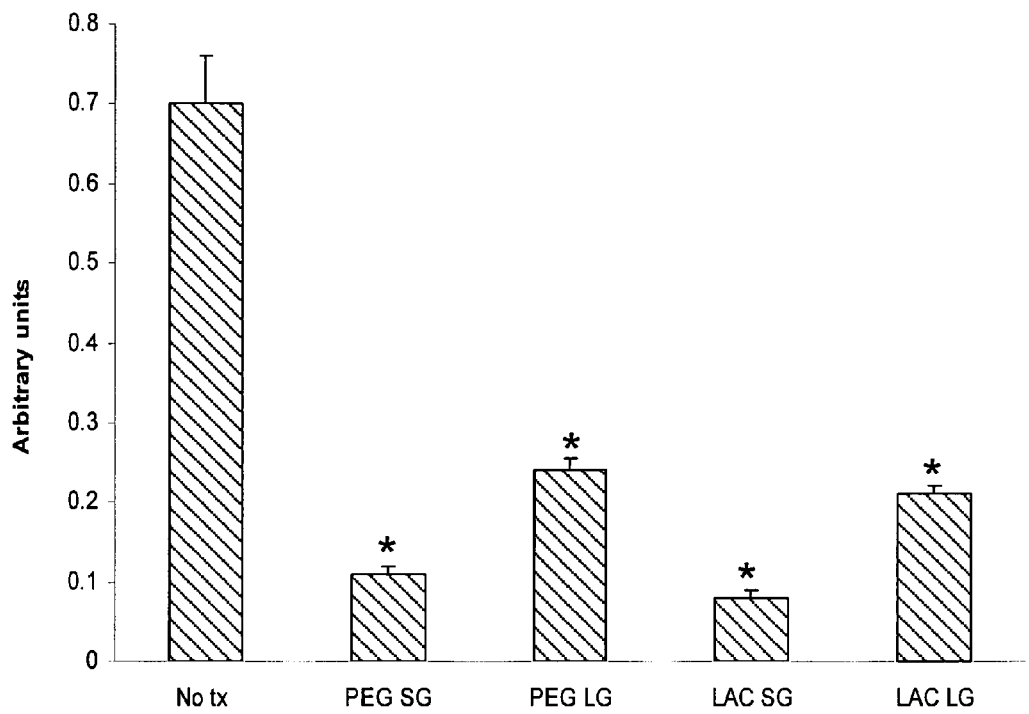
FIG. 9A illustrates the effect of DOPA-containing gels of the present invention on human dermal fibroblast cell motility.
Figure 9B:
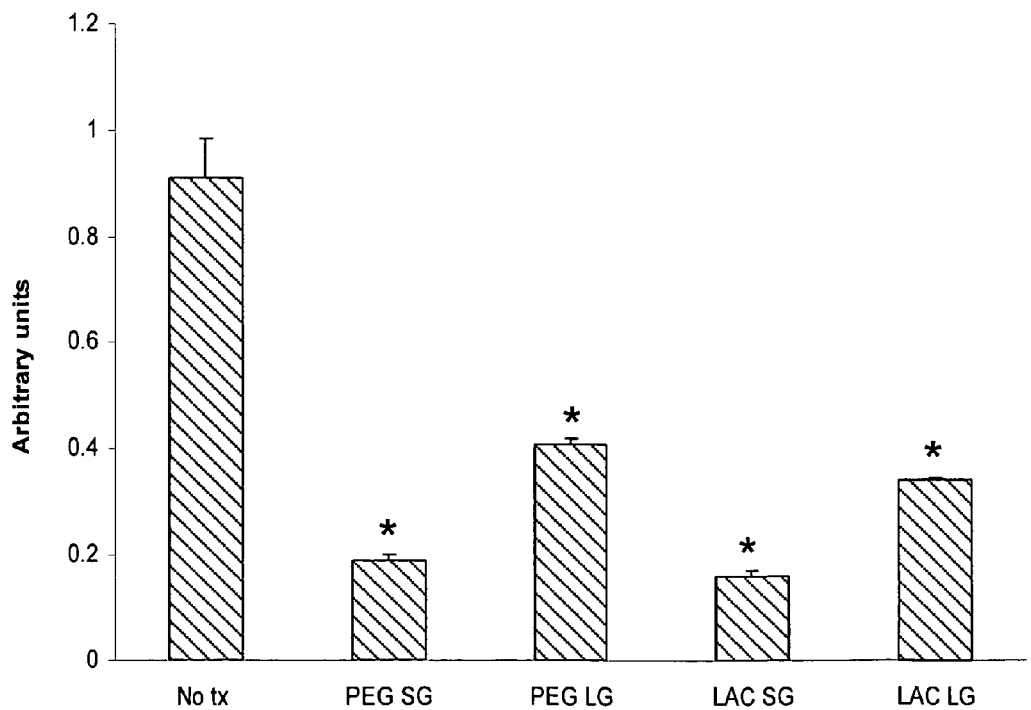
FIG. 9B illustrates the effect of DOPA-containing gels of the present invention on human dermal keratinocyte cell motility, wherein the gel composition was as described in connection with FIGS. 7A and 7B, wherein cells were exposed to gels after 48 hours in serum depleted media and motility assessed by an in vitro wound healing assay, and values are expressed as mean+/−SEM. (n=3), *=p<0.05 compared to diluent alone (No tx).
Figure 10A:
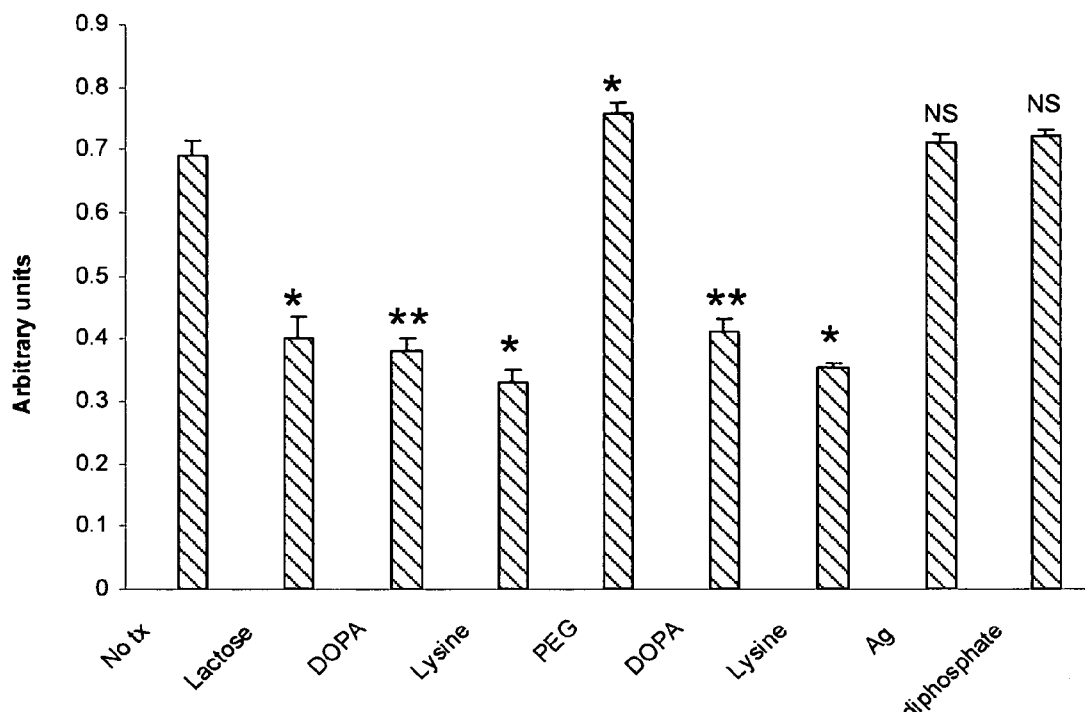
FIG. 10A illustrates the effects of individual components of the DOPA-containing gels of the present invention on human dermal fibroblast cell motility.
Figure 10B:
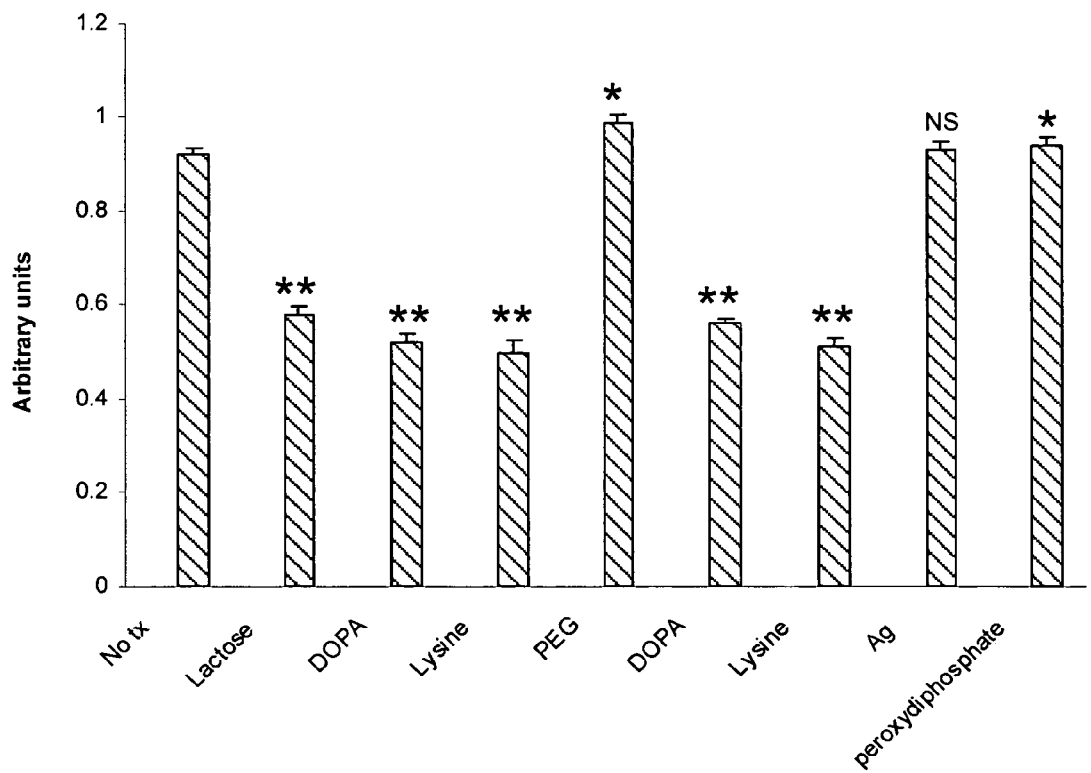
FIG. 10B illustrates the effects of individual components of the DOPA-containing gels of the present invention on human dermal keratinocyte cell motility, wherein the cells were exposed to gels after 48 hours treatment in serum depleted media and motility assessed by an in vitro wound healing assay, and values are expressed as mean+/−SEM. (n=3), NS=Not significant, *=p<0.05, **=p<0.01 compared to diluent alone (No tx).

Wound healing further requires active migration of the structural cells into the defect, and in the case of a wound network, matrix or gel, into the gel to replace the wound healing matrix. Gels formed from lactose (LysDOPA)$_8$ or DLL and PEG (LysDOPA)$_2$ or DLP prepolymers were found to limit the movement of both fibroblasts and keratinocytes (see FIGS. 9A and 9B). This limitation was noted with both gelated and liquid (pre-cured) gels, suggesting that multiple factors adversely affected cell movement. The limitation was confirmed by examining cell migration in the face of individual components, and finding that lactose, L-DOPA, and LDI all limited cell movement (see FIGS. 10A and 10B).

In the present invention, the adverse impact on cell function was ameliorated or corrected by addition of a biologically active agent or bioactive agent (via a biological component as described above) to the synthetic component polymeric network to produce a hybrid polymeric network Without limitation to any mechanism, we hypothesized the limiting effect on cell migration was as likely to be physiochemical as molecular, and thus not be avoided by simple component replacement approaches.

In several embodiments of the present invention the protein collagen was covalently incorporated into the wound healing polymer matrices of the present invention. Fibrillar collagen is a component of skin extracellular matrix. Collagen is used clinically and is amenable to industrial production parameters. Collagen is important for cell attachment and proliferation. It is involved in a number of biological events, including organogenesis in early development, and wound healing. The first phase of wound healing is hemostasis, or the stoppage of bleeding. Collagen is an efficient hemostatic agent because it allows platelets adhesion and aggregation, as well as the release of soluble clotting factors. Collagen, either alone or in combination with other materials, is also frequently used in tissue engineering applications such as vascular prostheses and artificial organs.

Figure 11A:
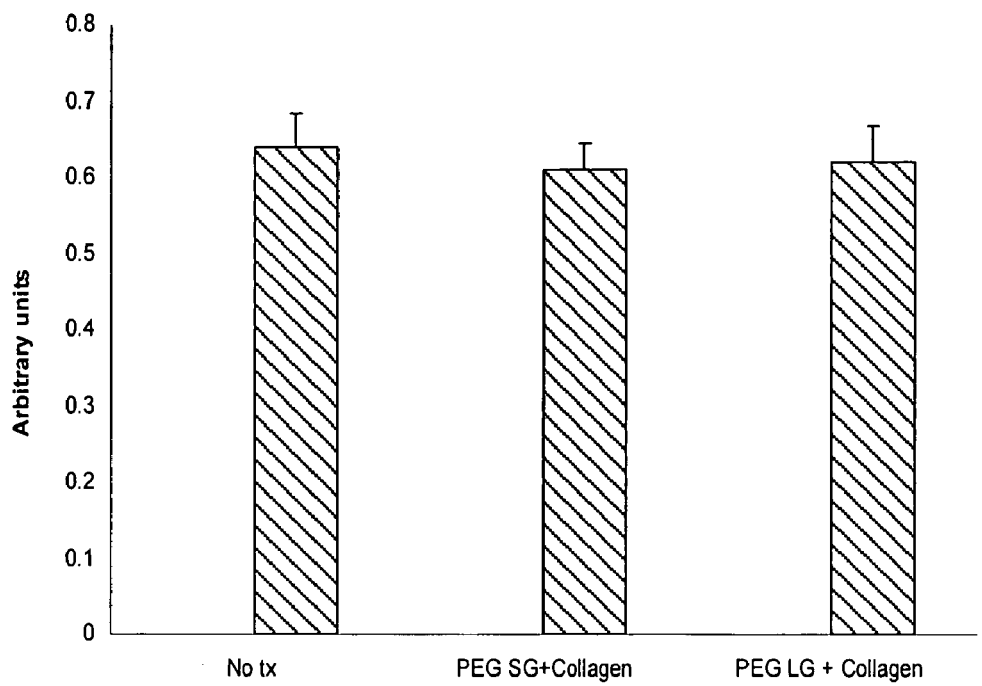
FIG. 11A illustrates the effect of DOPA-containing gels of the present invention with collagen on human dermal fibroblast cell motility.
Figure 11B:
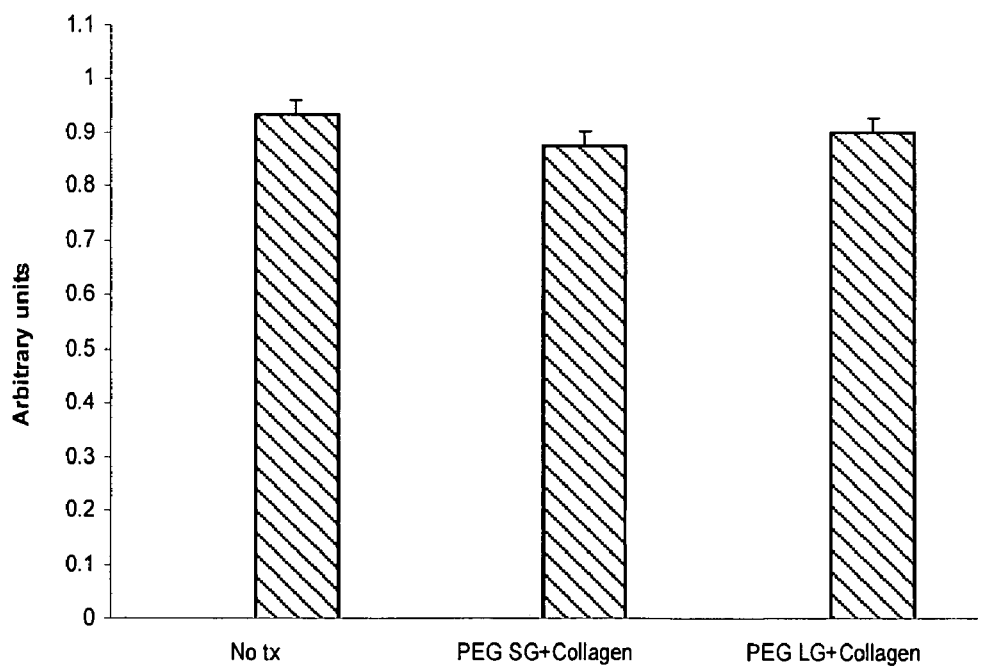
FIG. 11B illustrates the effect of DOPA-containing gels of the present invention with collagen on human dermal keratinocyte cell motility, wherein cells were exposed to gels (PEG SG-solid gel having PEG, LDI, DOPA, Ag, and peroxydiphosphate; PEG LG-liquid gel having PEG, LDI, and DOPA; both with collagen) after 48 hours treatment in serum depleted media, cell motility was assessed by in vitro wound healing assay, and values are expressed as mean+/−SEM. (n=3).

In several studies, it was demonstrated that covalent incorporation of collagen I fibers in the PEG gel compensated for the migration inhibition (see FIGS. 11A and 11B) described above, resulting in movement statistically not different from that in the absence of any gel.

Figure 12A:
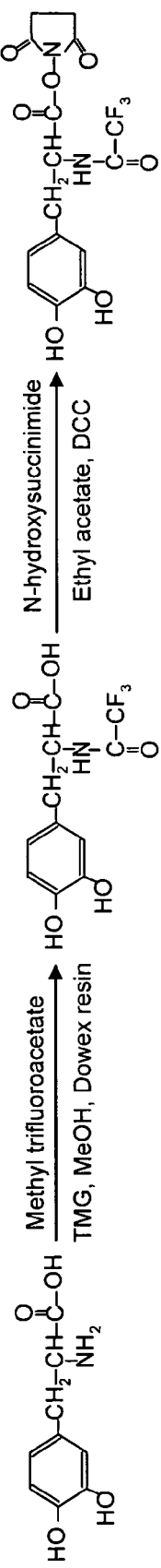
FIG. 12A illustrates protection of the amine group of DOPA and reaction of the protected DOPA with N-hydroxysuccine to synthesize an active DOPA.
Figure 12B:
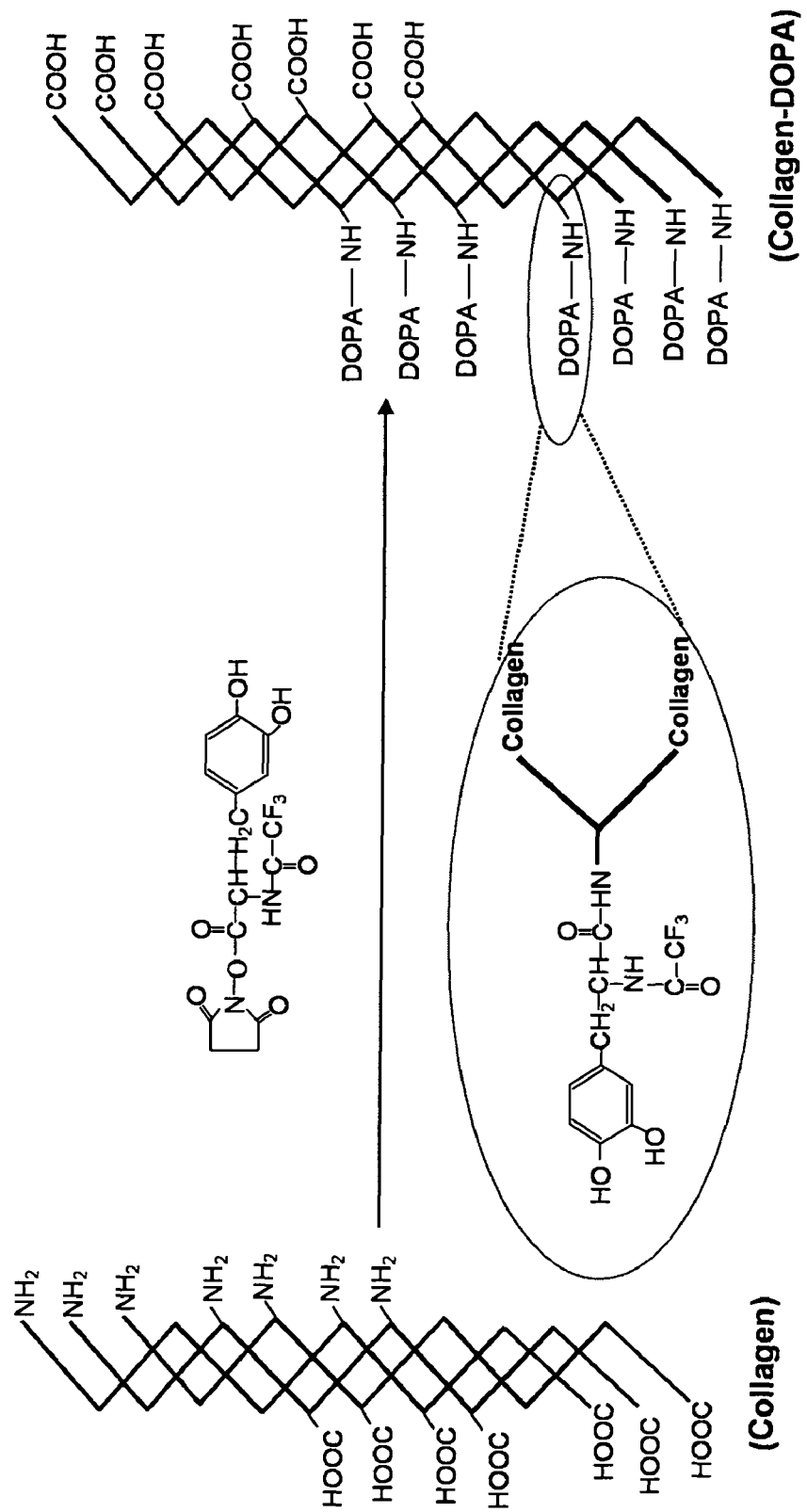
FIG. 12B illustrates conjugation of active DOPA with collagen to synthesize DOPA-rich collagen.
Figure 12C:
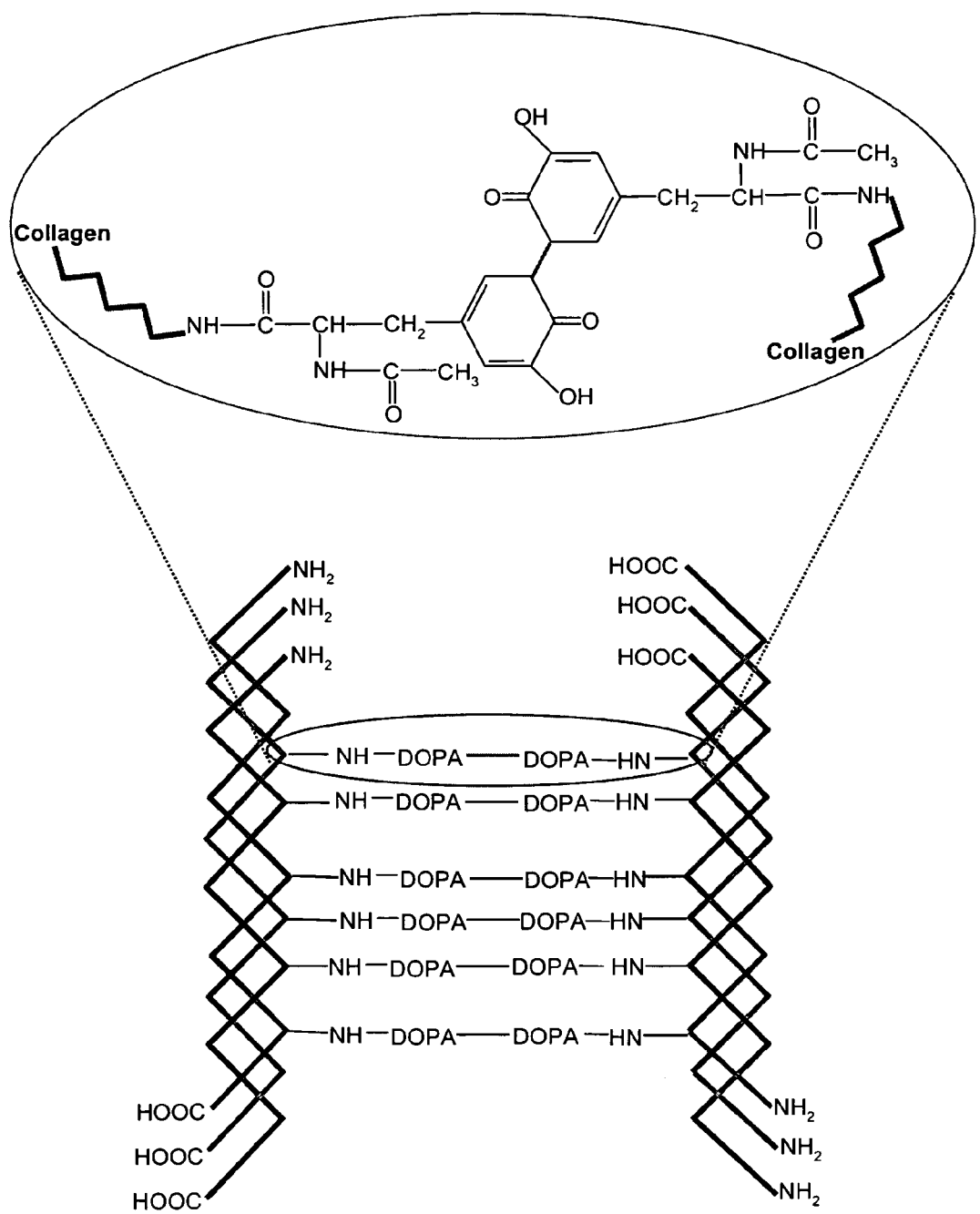
FIG. 12C illustrates crosslinking pathways for DOPA-containing collagen.

In several embodiments, collagen was covalently incorporated into the polymer networks of the present invention by first covalently attaching or conjugating collagen with DOPA and then curing such DOPA-collagen polymers as described above. Two different schemes were used to synthesize two different types of DOPA-collagen polymers. In a first synthetic scheme, illustrated in FIGS. 12A through 12C, a DOPA and collagen only conjugate was synthesized. In this reaction scheme, the amine group in DOPA was first protected using trifluoroacetate. The protected DOPA was then reacted with N-hydroxysuccine to synthesize an active DOPA as illustrated in FIG. 12A. The active DOPA was then reacted with collagen as illustrated in FIG. 12B to synthesize a DOPA rich collagen. FIG. 12C illustrates cross-linking pathways for such DOPA-containing collagen. The protected amine of the DOPA can be unprotected (using techniques known in the chemical arts) or remain protected before polymerization.

Figure 13A:
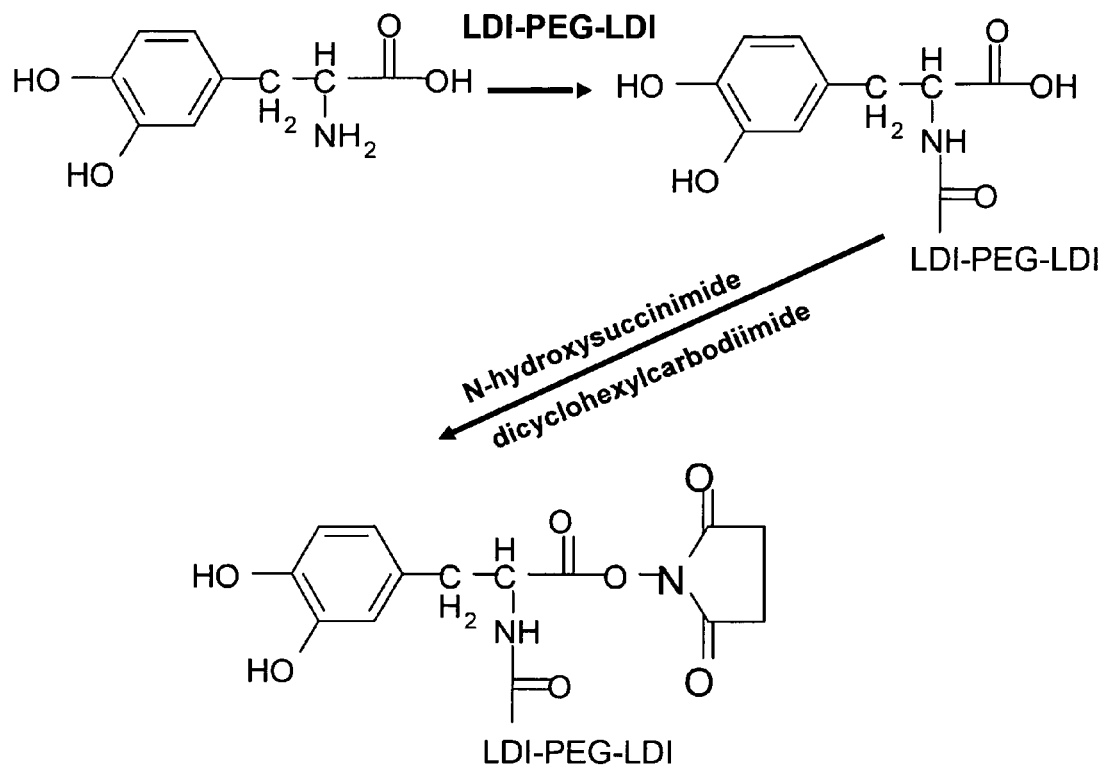
FIG. 13A illustrates a route to synthesis of a DOPA-containing collagen.
Figure 13B:
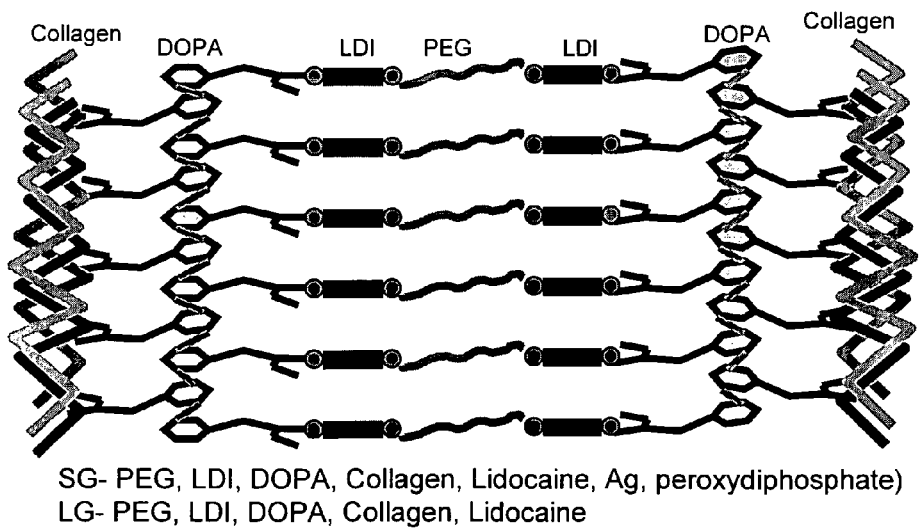
FIG. 13B illustrates a prepolymer formed using LDI, PEG and DOPA, wherein the DOPA is activated and conjugated with collagen.

As illustrated in FIGS. 13A and 13B, in a second synthetic scheme, a prepolymer is formed using, for example, LDI and a core molecule such as PEG. DOPA can, for example, be reacted with an LDI-PEG-LDI prepolymer to get DOPA-LDI-PEG-LDI-DOPA prepolymer. The DOPA-containing prepolymer can then be reacted with N-hydroxysuccine and collagen as described above. As the amine group of DOPA is reacted with the LDI-PEG-LDI prepolymer, there is no need to deprotect the amine group as described above.

In several studies, because of the high cost of commercial soluble collagen and the poor reactivity of insoluble collagen, we isolated and purified type I collagen from rat skin. Such isolated rat skin collagen showed four major peaks matching the standard collagen sample obtained from Sigma on carboxymethyl (CM)-cellulose chromatography. Amino acid analysis indicated that the number of glycyl residues in each α chain is highly conserved at approximately one-third of the total amino acid residues (data not shown). SDS-PAGE showed characteristic bands of type I collagen, namely α1(I), α2(I), β11(I), β12(I) and γ(I). These results indicated type I collagen had been successfully isolated and purified from rat skin.

The structure of activated DOPA as synthesized in FIG. 12A was confirmed by electrospray mass spectrometry. Tandem mass spectrometric analysis of m/z peak 391 (M+H) gave daughter ion peaks consistent with the expected fragmentation pattern of this compound.

Activated DOPA was chosen as the coupling agent because it contained one N-hydroxysuccinimide which was able to react specifically with primary amines present on the collagen as illustrated in FIG. 12B. The link belts represented the triple helical domains of collagen and the structure detail of modified collagen and shown in FIG. 12B. Typically, other reactions of this type are completed at pH 9, wherein greater substitution can occur. However, in the studies of the present invention, the reaction was performed in PBS buffer (pH 5) at room temperature to prevent the spontaneous fibrillogenesis of collagen that can occur at neutral pH. Excess activated DOPA was removed from the reaction mixture by dialysis. Amino acid analysis indicated that 76 nmol DOPA has combined with 5 mg of collagen. Larger molecular weight bands of proteins were found in the sample of collagen modified with DOPA compared to untreated collagen.

DOPA-containing pre-polymer for reaction with DOPA-containing collagen was synthesized in a two-step reaction using PEG as the core molecule as described above. As also described above, silver nitrate and potassium peroxydiphosphate were used to initiate polymerization of the prepolymers. FIGS. 3B and 12C, for example, illustrate cross-linking pathways for the DOPA-containing compounds.

Figure 14:
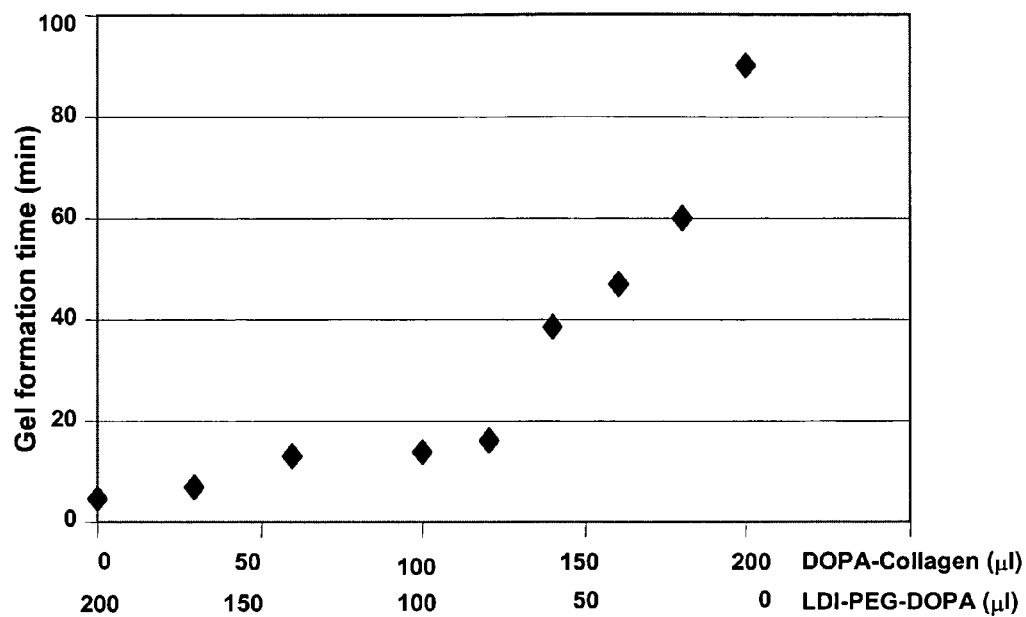
FIG. 14 illustrates a study of curing time of DLP-DOPA-collagen gel as measured at various amounts of DLP (DOPA-LDI-PEG) polymer (0.3 g/ml) and DOPA-modified collagen (5 mg/ml), wherein the total volume of the mixture was 200 µl.

Concentration of DOPA-modified collagen affected the gel cure time as illustrated in FIG. 14 Cure time increased as the ratio of DOPA-collagen to DLP pre-polymer increased. Without limitation to any mechanism, an explanation is that the concentration of DOPA-collagen solution (5 mg/ml) was much lower than that of DLP pre-polymer (0.3 g/ml). The cure time of DOPA-collagen gel was shorter than that of collagen gel without DOPA treatment.

Collagen was stained by Sirius red in the DOPA-collagen gel and DLP-DOPA-collagen gel. As expected, gel made of DLP polymer only did not become stained.

Figure 15:
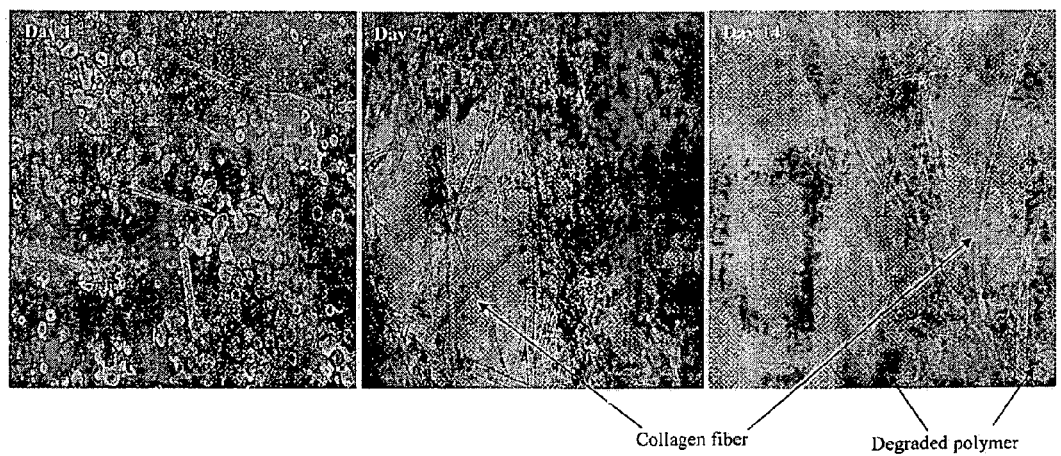
FIG. 15 illustrates a study of the degradation of the DLP-DOPA-collagen gel as determined in tissue culture medium (DMEM) at 37° C., wherein the gel was made by 0.5 ml DOPA-modified collagen (5 mg/ml) and 5 ml of DLP polymer solution (0.3 g/ml) using 50 µg of $AgNO_3$ and 50 µg $K_4P_2O_8$ as initiators, and wherein the gel completely degraded in 30 days.
Figure 16A:
FIG. 16A illustrates studies of human skin fibroblasts grown on the collagen gel for DOPA-modified collagen gel.
Figure 16B:
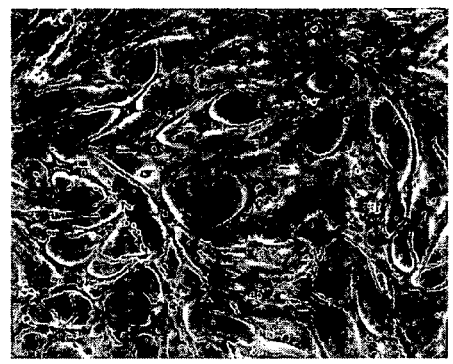
FIG. 16B illustrates studies of human skin fibroblasts grown on the collagen gel for DLP and DOPA-modified collagen gel.
Figure 16C:
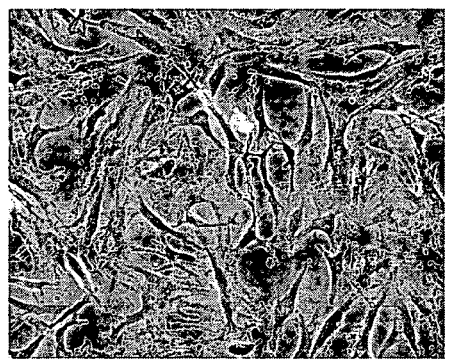
FIG. 16C illustrates studies of human skin fibroblasts grown on the collagen gel for DLP polymer gel.
Figure 16D:
FIG. 16D illustrates that MTT assay cell proliferation significantly increased when grown on collagen-containing gels compared to the tissue culture plate or gel without collagen.
Figure 16E:
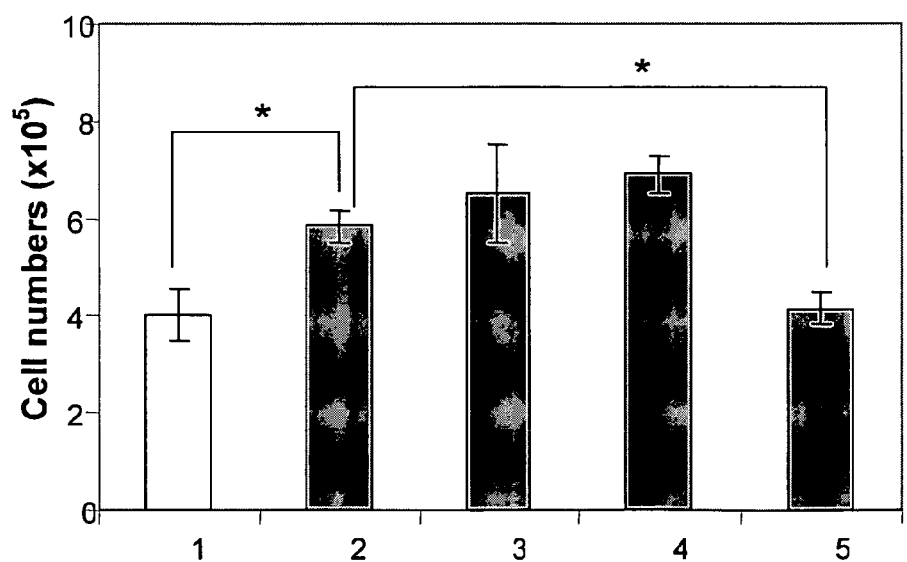
FIG. 16E illustrates: in column 1, the cells grown on the tissue culture plate; in column 2, cells grown on DOPA-collagen gel; in column 3: cells grown on collagen gel; in column 4, cells grown DOPA-collagen and DOPA-LDI-PEG gel; and in column 5, cells grown on DOPA-LDI-PEG gel ($*p<0.05$).

DLP-DOPA-collagen gel was also demonstrated to be degradable. Collagen fiber remained when the gel degraded. Among the other degradation products were lysine, PEG, DOPA, silver and phosphate. DLP-DOPA-collagen gel degraded more slowly than the gel made of DLP polymer only as illustrated in FIG. 15.

Fibroblast is the main cell type of the dermal layer. Proliferation of human skin fibroblasts was enhanced when grown on the collagen-containing gel as compared to growth on a tissue culture plate. A similar result was found in DLP-DOPA-collagen gel as illustrated in FIG. 16A through 16E. MTT results indicate that fibroblast grown on DOPA-containing polymer gel showed similar viability to that grown on a tissue culture plate ($p>0.05$). Cell viability increased on collagen gel, DOPA-conjugated collagen or collagen-DLP polymer ($p<0.02$). Once again, incorporation of collagen I fibers in the PEG gel improved cell migration (see FIGS. 11A and 11B) resulting in cell proliferation statistically not different from that in the absence of any gel. The collagen-containing polymer gel was also more flexible than polymer-gel formed without collagen.

We noted that gels could be formed at all ratios of collagen (biological component)/synthetic component, although the curing time increased significantly as the amount of collagen increased. Without limitation to any mechanism, this effect is likely a result of concentration rather than any inherent limitations of the derivatized collagen. Because collagen is difficult to dissolve in buffer, a more dilute solution (as compared to the synthetic) must be employed, meaning that the concentration of reactive end groups is substantially smaller where collagen is concerned. Given that the crosslinking reaction is at least first order in reactive group concentration, it is understandable that the gel time increases as the collagen fraction increases. In buffer (in vitro), only the synthetic portion of the polymer degrades, leaving behind a primarily collagen skeleton after 14 days. Not surprisingly, we have found that fibroblasts increasingly thrive as the collagen fraction in the gel increases. These gels not only did not retard fibroblast and keratinocyte motility and proliferation, but actually promoted it.

Figure 17:
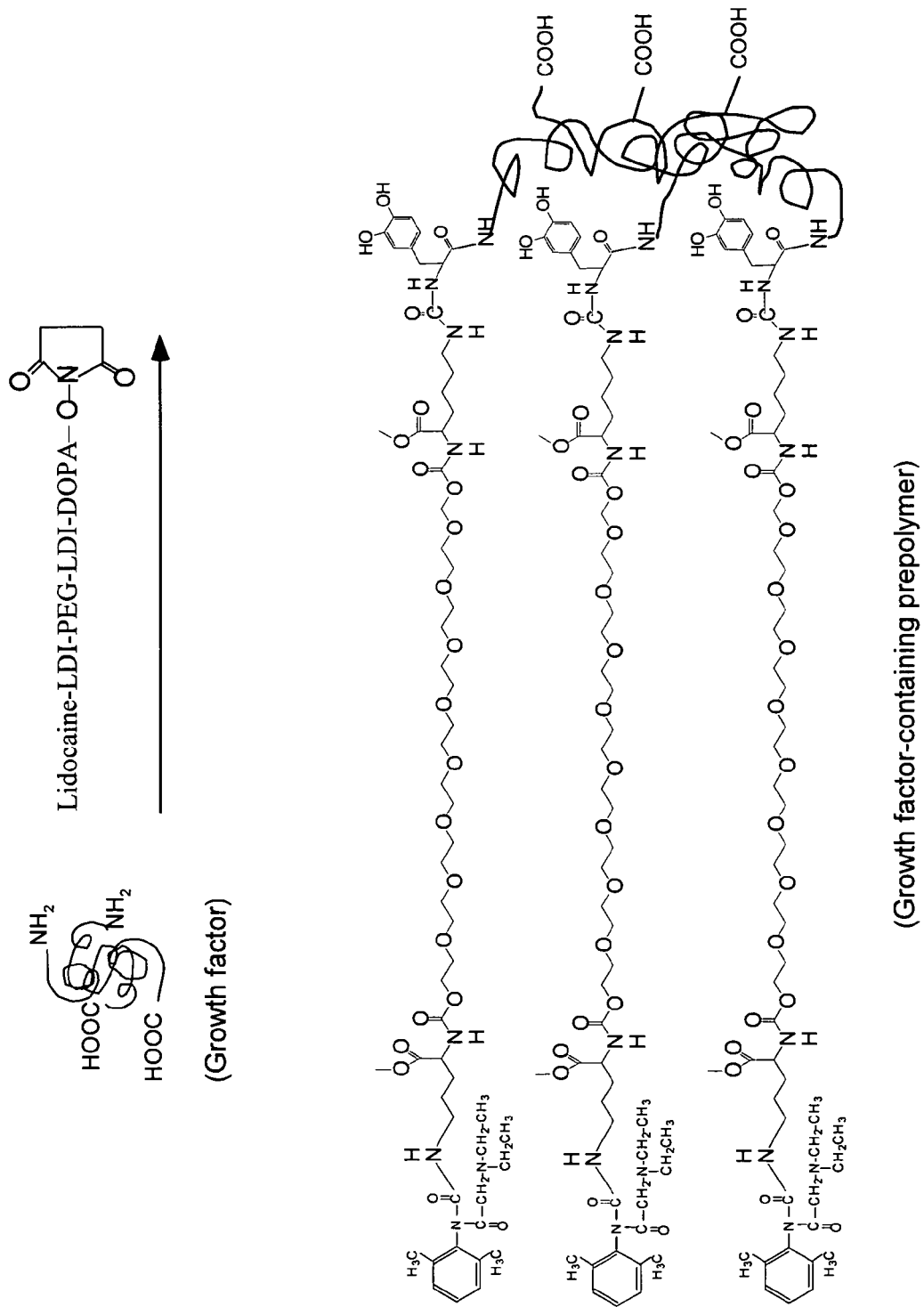
FIG. 17 illustrates an representative synthetic scheme for covalent incorporation of a biologically active molecule such as a growth factor into the polymer matrices of the present invention.

Other biologically active agents are readily incorporated into the polymer matrices of the present invention. For example, various cell growth factors can be incorporated. Examples of growth factors include EGF, TGFalpha or TGFa, PDGF, VEGF, FGFs, IGF-1, HGF, KGF, TGFbeta (1,2,3) or TGFb, CXCR3 ligands (CXCL9, CXCL10, CXCL11), IL-10 and IL-4. As illustrated in FIG. 17, growth factors can readily be covalently incorporated into the polymers of the present invention by, for example, reaction of amine groups thereof with active DOPA (either alone, or conjugated with, for example, an LDI-containing material).

As used herein, the terms "biologically active" or "bioactive" refers generally to an agent, a molecule, or a compound that affects biological or chemical events in a host. Biologically active or bioactive agents may be synthetic molecules, biomolecules, or multimolecular entities and include, but are not limited to, proteins (including, but not limited to, collagen, fibrin/fibrinogen, fibronectin, entactin, tenascin and enzymes (including, but not limited to, MMPs, TIMPs, proteinases, phospholipases, plasmin/plasminogen, lipases, and lysyl oxidase, a crosslinking agent for collagen)), organic catalysts, ribozymes, organometallics, glycoproteins (for example, proteoglycan), glycosaminoglycans (for example, hyaluronic acid or HA), peptides, polyamines, polyamino acids, antibodies, nucleic acids, steroidal molecules, antibiotics, antivirals, antimycotics, anticancer agents, analgesic agents, antirejection agents, immunosuppressants, cytokines, carbohydrates, oleophobics, lipids, extracellular matrix and/ or its individual components (such as collagen etc.), growth factors, hemostatic agents (including, for example, small molecules such as ATP and epinephrine and derivatives thereof), pharmaceuticals, chemotherapeutics, and therapeutics. Cells and non-cellular biological entities, such as viruses, virenos, virus vectors, and prions can also be bioactive agents.

In general, the wound healing networks, matrices or gels of the present invention include a bio-compatible polymer backbone which, for example, provides stiffness and flexibility to the gel. The wound healing matrix should be sufficiently flexible or compliant to deform with the surrounding deformation of tissue during movement and compression. However, the healing matrix should also be sufficiently stiff to support cell migration and proliferation. For example, the modulus can be in the range of approximately 10 to approximately 60 Pa. Compression of matrices and gels often depends on hydration, which is modulated not only by the polymer backbone, but also by various biological components such as HA and proteoglycans that can be incorporated into the wound healing matrices of the present invention.

Certain preferred bioactive agents for incorporation into the wound healing matrices of the present invention include, but are not limited to, those beneficial for hemostasis, adhesion of fibroblasts, epithelial cells and endothelial cells (the latter for angiogenesis), analgesia, cell survival and proliferation, and antimicrobial function. Hemostatic agents include matrix components including, but not limited to, collagen, fibronectin, fibrin, plasmin/plasminogen and small molecules such as epinephrine and ATP. Adhesion molecules can, for example, include sites for binding of the beta1 and beta3 integrin types prevalent on adherent cells; examples include, but are not limited to, collagen, fibronectin, collagen and their small peptide derivatives of RGD-containing and synergistic sites. These adhesion-promoting molecules will also provide for cell migration and invasion into the gel, which is important for repair/replacement and angiogenesis. Analgesia can be provided by incorporating known therapeutic analgesics such as those in the lidocaine family (as described below). Cell survival and proliferation can, for example, be controlled by incorporated growth factors and cytokines including, for example, VEGF, EGF, TGFa, FGFs (all of which are angiogenic), TGFb (which is chemotactic) and IGF and PDGF (for survival signals). Further, in addition to the antimicrobial effects of the initiating agent silver, other antimicrobials can be incorporated to prevent foreign body colonization. All classes of antimicrobials can be incorporated. Broad spectrum antimicrobials such as macrolides, topoisomerase inhibitors, and cephalosporins can be preferred.

Biologically active agents incorporated into the wound healing matrices of the present invention preferably maintain their biologically activity while covalently bonded within the wound healing matrix and/or after degradation of the matrix. The present inventors have generally found that biologically active agents retain their biological activity after covalent incorporation under the relatively benign conditions of the reactions of the present invention.

Biologically active agents with reactive functionalities such as an amine group can readily be reacted with, for example, active DOPA for covalent incorporation. Likewise, biologically active agents with at least one active hydrogen can readily be reacted with an isocyanate group such as present in LDI. Once again, examples of chemical moieties with an active hydrogen include primary and secondary amine groups, hydroxyl groups and thiol groups.

For example, in addition to incorporation of collagen into the wound healing matrices of the present invention, a liquid form of extracellular matrix produced from porcine urinary bladders was also incorporated in other wound healing matrices of the present invention. In those studies, porcine urinary bladders were harvested from pigs immediately following euthanasia. Connective tissue and adipose tissue were removed from the serosal surface and any residual urine was removed by repeated washes with tap water. The tunica serosa, tunica muscularis externa, and the tunica submucosa were mechanically removed and the luminal urothelial cells of the basement membrane were dissociated by soaking in 1.0 N saline solution yielding a biomaterial composed of the basement membrane plus the subjacent tunica propria. This bi-laminate structure was referred to as urinary bladder matrix or UBM. UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. UBM sheets were subsequently lyophilized and powdered. One gram of lyophilized UBM powder and 100 mg of pepsin were both mixed in 100 mL of 0.01 M HCL. The solution was kept at a constant stir for ~48 hrs at room temperature (25 C). After pepsin digestion, the digest was aliquoted and stored at −20 C until use or at 4 C after initial thawing.

Figure 18A:
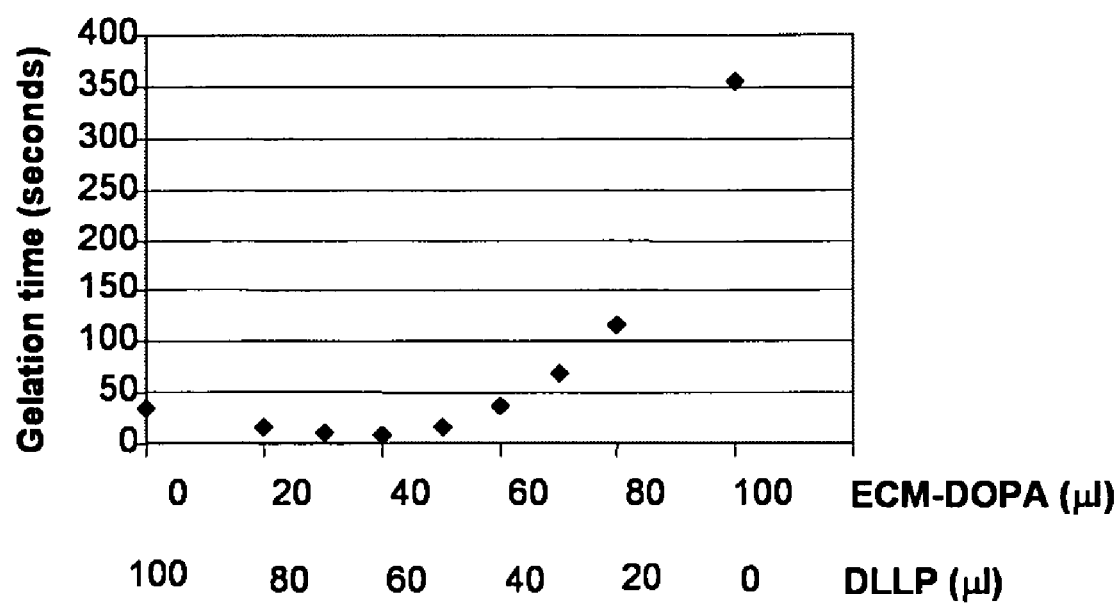
FIG. 18A illustrates gelation testing using ECM-DOPA (ECM=extracellular matrix; 1 ml of 5 mg/ml ECM reacted with 100 μl of 2 μmol/ml BOC-DOPA-NHS) and DLLP (0.34 g Lactose-1.6 ml LDI-0.8 g DOPA-1.6 g PEG 400; dialyzed and dissolved in 25 ml of 0.1 M $Na_2B_4O_7$), initiated by each 10 μl of 10 mg/ml $AgNO_3$ and $K_4P_2O_8$.

The liquid extracellular matrix was conjugated with L-DOPA using the same procedure as described above for collagen. This conjugate was then mixed with synthetic component materials (a DOPA-terminal PEG-lactose blend) in varying proportions. Cure was again initiated using potassium peroxydiphosphate and silver. Cure results are illustrated in FIG. 18A. Much faster curing than for collagen (possibly as a result of the presence of the lactose precursor, which exhibits a functionality of 8) and synergy between the extracellular matrix and the synthetic component, such that mixtures of the two cured faster than either alone, was observed. At an optimal concentrations of extracellular matrix and synthetic, cure was complete in less than 10 seconds.

Figure 18B:
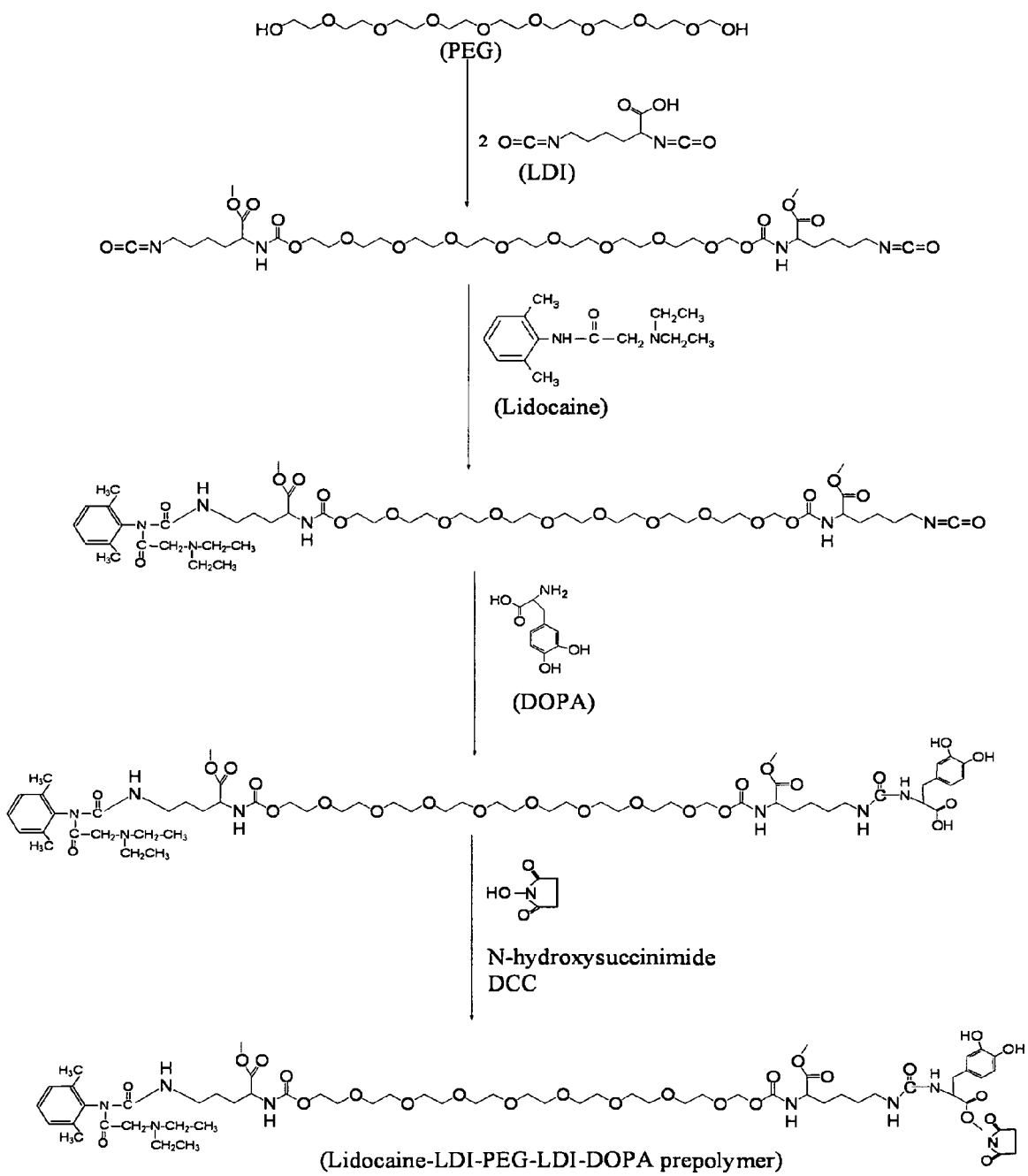
FIG. 18B illustrates the incorporation of lidocaine into the polymer matrices of the present invention.

Further, FIG. 18B illustrates reaction of the secondary amine group of lidocaine with an isocyanate functionality of LDI modified PEG in which the analgesic or anesthetic lidocaine was incorporated into a prepolymer of the present invention.

Biologically active agents and other agents (including, for example, those without reactive groups for covalent incorporation) can also be noncovalently incorporated into the polymer matrices of the present invention, from which they can, for example, diffuse to provide desired effects. For example, the antimicrobial effects of silver incorporated into the polymeric wound healing matrices of the present invention are described above and further described below.

An anesthetic such as one of the lidocaine topical anesthetic family can also be noncovlently incorporated into the polymer matrix. Such physical incorporation, wherein the agent is entrapped within the matrix during gelation, can result in quicker release from the matrix than would be the case in covalent incorporation. Traumatic wounds are commonly painful and limit functionality beyond the physiologic extent of the wound. Narcotic analgesics relieve pain by acting centrally on the nervous system. Although effective in pain control, they may alter one's sensorium, resulting in reduced effectiveness (for example, on the battlefield). Addition of a topically effective local anesthetic molecule provides for a reduction in pain at the wound site without the systemic side effects. By using controlled release technique(s) and long acting anesthetic agents, pain can be lessened for days.

Members of the lidocaine family of topical anesthetics are FDA-approved, well-tolerated, and chemically stable small molecules. Initial analgesia can, for example, be designed to occur within 15 minutes and last for 12-24 hours. The anesthetic agent can be selected based on length of action coupled with diffusion from the gel solution. For example, if the diffusion rate from the gel provides for 24 hour 'slow release' then one would choose an agent which is short-acting. However, if most of the anesthetic is delivered from the gel within the first few hours, one would incorporate a long-acting molecule.

Figure 19A:
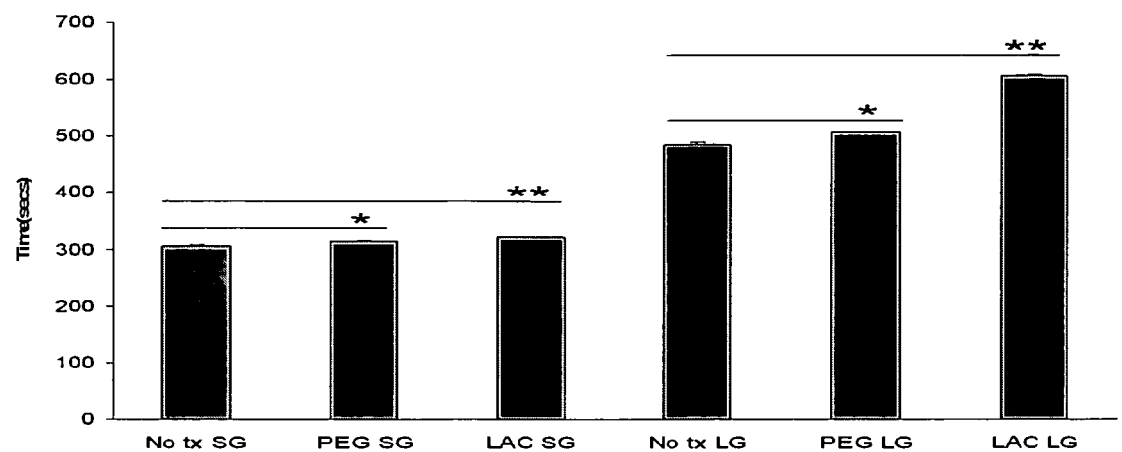
FIG. 19A illustrates the effect of DOPA-containing gels of the present invention on clotting time.
Figure 19B:
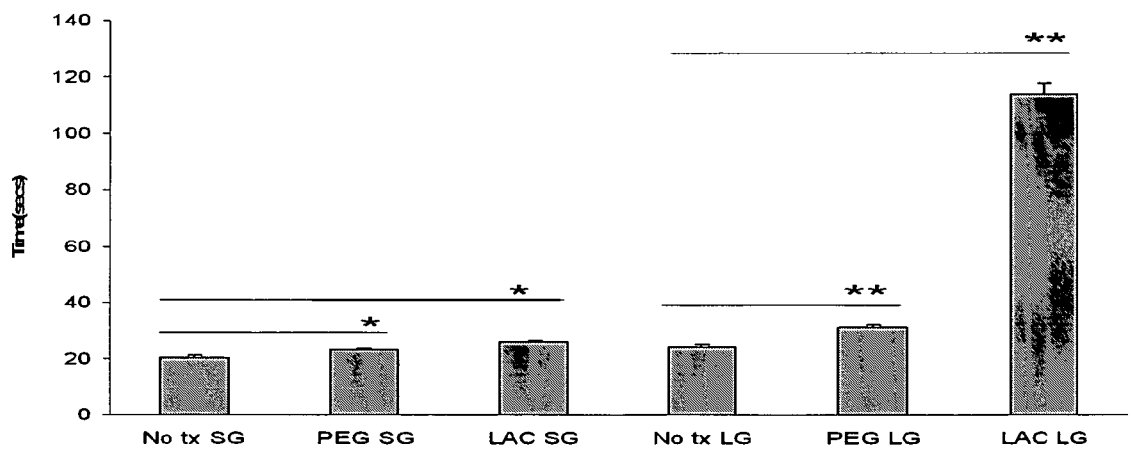
FIG. 19B illustrates the effect of DOPA-containing gels of the present invention on prothrombin time.
Figure 19C:
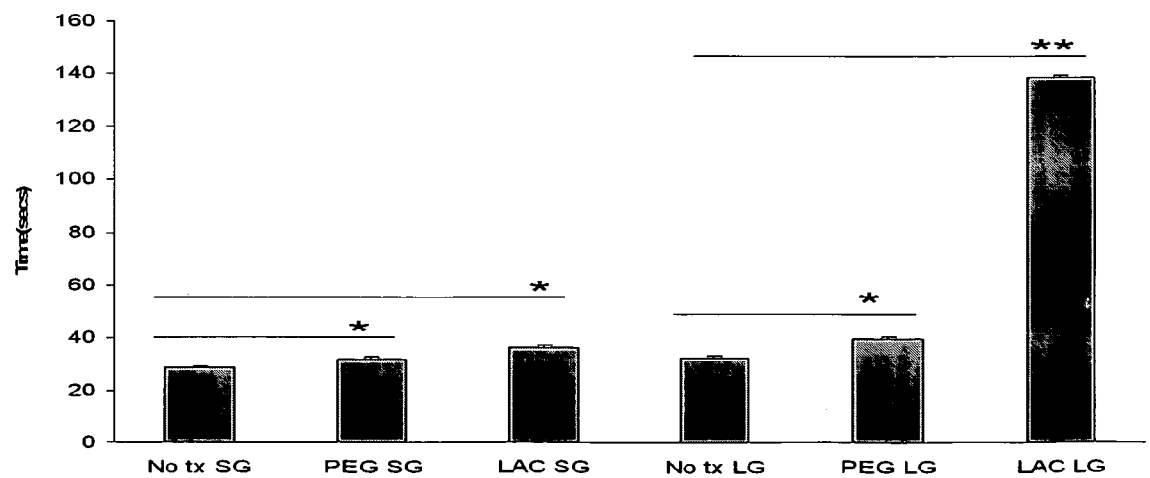
FIG. 19C illustrates the effect of DOPA-containing gels of the present invention on partial thromboplastin time as assessed by the tube method, wherein gel composition in the studies of FIGS. 19A, 19B and 19C was as described previously above, values are expressed as mean+/−SEM. (n=3), $*=p<0.05$, $**=p<0.01$, and bars above the graphs indicate the groups compared.

As the gels of the present invention are designed to be placed in wound fields in which bleeding occurs, hemostasis is preferably enabled. The PT, aPTT, and clotting time of human blood were within the normal range in the presence of the solid PEG and Lactose gels (without collagen) as illustrated in FIGS. 19A, 19B and 19C, respectively. As the gel will be introduced into the wound in the pre-gelated liquid or flowable form, the gels were also tested in liquid, pre-cured form. While the liquid, pre-cured PEG gel demonstrated slightly elongated hemostatic parameters, these were not statistically different from the dilutional effect of a 25% volume addition (no tx LG), and were thus considered not a concern. However, the liquid, pre-cured Lactose gel compromised all three hemostatic responses beyond the dilutional effect. The detrimental effectx of the lactose gel can likely be ameliorated or corrected via incorporation of a biological components that includes a hemostatic agent (for example, collagen).

The antimicrobial aspects of the PEG and lactose gels were studied as models to determine the effects of incorporation of silver into the polymer matrices of the present invention. Despite the well documented antimicrobial effects of silver, the question of whether Ag would be released from the gel to function as an antimicrobial had to be demonstrated, as did its relative non-toxicity to the resident skin cells. It was found that both lactose and PEG polymer discs demonstrated inhibition of the growth of *M. luteus* and all of other test organisms as set forth Table 1. The PEG gel presented larger zones of inhibition with one exception. However, both gels provided for greater inhibition than the Ag-impregnated filter paper control.

TABLE 1

| Microorganism | Control (1% AgNo3) | PEG, LDI, DOPA, Ag peroxydiphosphate | Lactose, LDI, DOPA, Ag, peroxydiphosphate |
|---|---|---|---|
| *M. luteus* | 18 | 50 | 22 |
| *S. aureus* | 15 | 36 | 21 |
| *S. pyogenes* | 14 | 36 | 22 |
| Diphtheroids | 15 | 23 | 31 |
| *P. aeruginosa* | 13.5 | 37 | 22 |
| *E. coli* | 15 | 35 | 21 |
| *Acinetobacter* | 16 | 33 | 27 |
| *C. perfringens* | 14 | 25 | 23 |
| *B. subtilis* | 13 | 35 | 21 |
| *C. albicans* | 16 | 38 | 23 |

In the studies of Table 1, zones of inhibition (in mm) were obtained with control and gels of either type as determined by the Disc Diffusion method. The microorganisms were streaked on individual blood agar plates. The PEG-containing gel included PEG, LDI, DOPA, Ag, and peroxydiphosphate as described above, The lactose-containing gel included Lactose, LDI, DOPA, Ag, and peroxydiphosphate as described above. Plugs for each gel type had silver concentration of 3.3 microgram, a diameter of 2 cm and a thickness of 1 mm. The control consisted of filter paper disc with a diameter of 1.25 cm and thickness of 1 mm and included 1% $AgNo_3$.

To determine the nature of the inhibition we assessed microbicidal and -static capacities as accomplished by one to three gel discs. The sensitivities of the agents varied as set forth in Table 2. A 3 log reduction in microbe number considering its initial count was taken as bactericidal activity. For all aerobic organisms significant antimicrobial activity was seen in the first 24 hours with both gels. Both the gels displayed a concentration dependant bactericidal action with *E. coli* and *P. aeruginosa* with more than 1 gel disc and bacteriostatic effect with 1 gel disc. With *A. baumanii* a time dependant antimicrobial activity was seen. All gram positive bacteria had similar time dependant kinetics. With *S. aureus* a two log reduction at 24 hours was seen when challenged with both gels. *S. pyogenes* and diphtheroids were similar in behaviour considering *S. aureus* except when challenged with three gel discs of either type where in a 3 log reduction was seen. With *C. albicans* the effect was found similar as with gram positive bacteria. With the anaerobes a time dependant antimicrobial activity was seen at 48 hours with both the gels.

TABLE 2

| Organism | Number of gel discs per tube | PEG containing gel Bacterial concentration at time: (CFU/ml) | | | Lactose containing gel Bacterial concentration at time: (CFU/ml) | | |
|---|---|---|---|---|---|---|---|
| | | 0 hours | 24 hours | 48 hours | 0 hours | 24 hours | 24 hours |
| S. aureus | 1 Disc | $2.5 \times 10^5$ | $1.86 \times 10^3$ | $1.72 \times 10^3$ | $2.5 \times 10^5$ | $2.18 \times 10^3$ | $2.06 \times 10^3$ |
| | 2 Discs | | $1.05 \times 10^3$ | $9.06 \times 10^2$ | | $1.96 \times 10^3$ | $1.55 \times 10^3$ |
| | 3 Discs | | $4.80 \times 10^2$ | $4.25 \times 10^2$ | | $1.01 \times 10^3$ | $9.05 \times 10^2$ |
| S. pyogenes | 1 Disc | $2.27 \times 10^5$ | $1.49 \times 10^3$ | $1.19 \times 10^3$ | $2.27 \times 10^5$ | $1.79 \times 10^3$ | $1.48 \times 10^3$ |
| | 2 Discs | | $1.01 \times 10^3$ | $6.05 \times 10^2$ | | $1.19 \times 10^3$ | $7.95 \times 10^2$ |
| | 3 Discs | | $2.55 \times 10^2$ | $1.55 \times 10^2$ | | $6.00 \times 10^2$ | $3.65 \times 10^2$ |
| Diphtheroid | 1 Disc | $2.33 \times 10^5$ | $5.80 \times 10^2$ | $4.25 \times 10^2$ | $2.33 \times 10^5$ | $8.45 \times 10^2$ | $6.85 \times 10^2$ |
| | 2 Discs | | $2.10 \times 10^2$ | 90 | | $5.35 \times 10^2$ | $3.90 \times 10^2$ |
| | 3 Discs | | 9 | 15 | | $3.10 \times 10^2$ | $2.35 \times 10^2$ |
| P. aeruginosa | 1 Disc | $2.28 \times 10^5$ | $5.95 \times 10^2$ | $1.80 \times 10^2$ | $2.28 \times 10^5$ | $8.20 \times 10^2$ | $3.85 \times 10^2$ |
| | 2 Discs | | 0 | — | | 0 | — |
| | 3 Discs | | 0 | — | | 0 | — |
| E. coli | 1 Disc | $2.32 \times 10^5$ | $1.36 \times 10^3$ | $8.95 \times 10^2$ | $2.32 \times 10^5$ | $1.98 \times 10^3$ | $1.52 \times 10^3$ |
| | 2 Discs | | 0 | — | | 0 | — |
| | 3 Discs | | 0 | — | | 0 | — |
| A. baumanii | 1 Disc | $2.35 \times 10^5$ | $9.15 \times 10^2$ | $7.85 \times 10^2$ | $2.35 \times 10^5$ | $1.13 \times 10^3$ | $9.80 \times 10^2$ |
| | 2 Discs | | $5.70 \times 10^2$ | $4.45 \times 10^2$ | | $7.65 \times 10^3$ | $6.45 \times 10^2$ |
| | 3 Discs | | $2.55 \times 10^2$ | $1.75 \times 10^2$ | | $5.05 \times 10^2$ | $3.75 \times 10^2$ |
| C. perfringens | 1 Disc | $2.38 \times 10^5$ | | $1.02 \times 10^3$ | $2.38 \times 10^5$ | | $1.39 \times 10^3$ |
| | 2 Discs | | | $7.10 \times 10^2$ | | | $9.06 \times 10^2$ |
| | 3 Discs | | | $3.85 \times 10^2$ | | | $6.05 \times 10^2$ |
| C. albicans | 1 Disc | $2.33 \times 10^5$ | $5.80 \times 10^2$ | $4.40 \times 10^2$ | $2.33 \times 10^5$ | $8.30 \times 10^2$ | $7.30 \times 10^2$ |
| | 2 Discs | | $3.00 \times 10^2$ | $2.00 \times 10^2$ | | $4.65 \times 10^2$ | $3.85 \times 10^2$ |
| | 3 Discs | | $1.55 \times 10^2$ | 35 | | $2.30 \times 10^2$ | $1.70 \times 10^2$ |

In Table 2, decrements in colony count upon challenge by the gels are set forth. Target microorganisms were seeded at $10^5$ colony forming units per ml. Parallel tubes were seeded with one to three gels. At 24 and 48 hours, the bacterial counts/concentrations in CFU/ml were determined. Anaerobic C. perfringens was counted only at 48 hours considering their normal growth patterns. Placement of a control tube having microorganisms at $10^5$ at 0 hour gave non log growth counts at 24 and 48 hours for aerobes and 48 hours for anaerobes. The composition of both gels were the same as described in connection with Table 1.

Figure 20A:
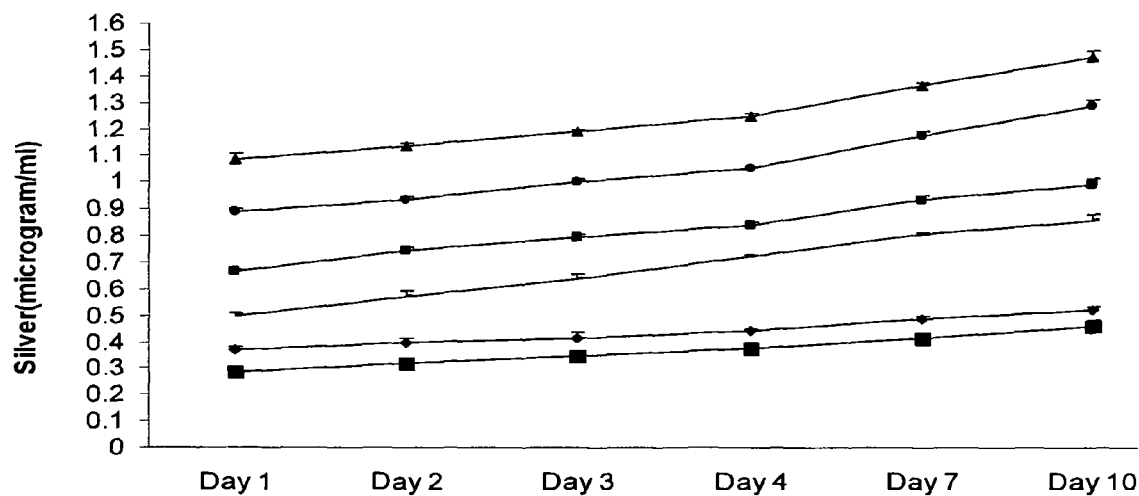
FIG. 20A illustrates of how silver leaches out of the gels over several days as determined by atomic absorption spectroscopy by showing cumulative silver concentration over a period of 10 days in broth in which the gels were immersed (one to three gels were tested).

Continued presence of Ag is preferred to keep a wound bed uninfected over time, while retention in the gel is preferred to prevent a foreign body nidus of infection. Ag was detected in the media increasingly with time as illustrated in FIG. 20A. The Ag rapidly leaves the PEG gel with 57% being detected in the media in 24 hours. This increased to 68% at day 4 and 80% by day 10. Leaching from the lactose gel was less than PEG gel with only 44% after one day, increasing to 58% at 4 days and 71% at 10 days.

Figure 20B:
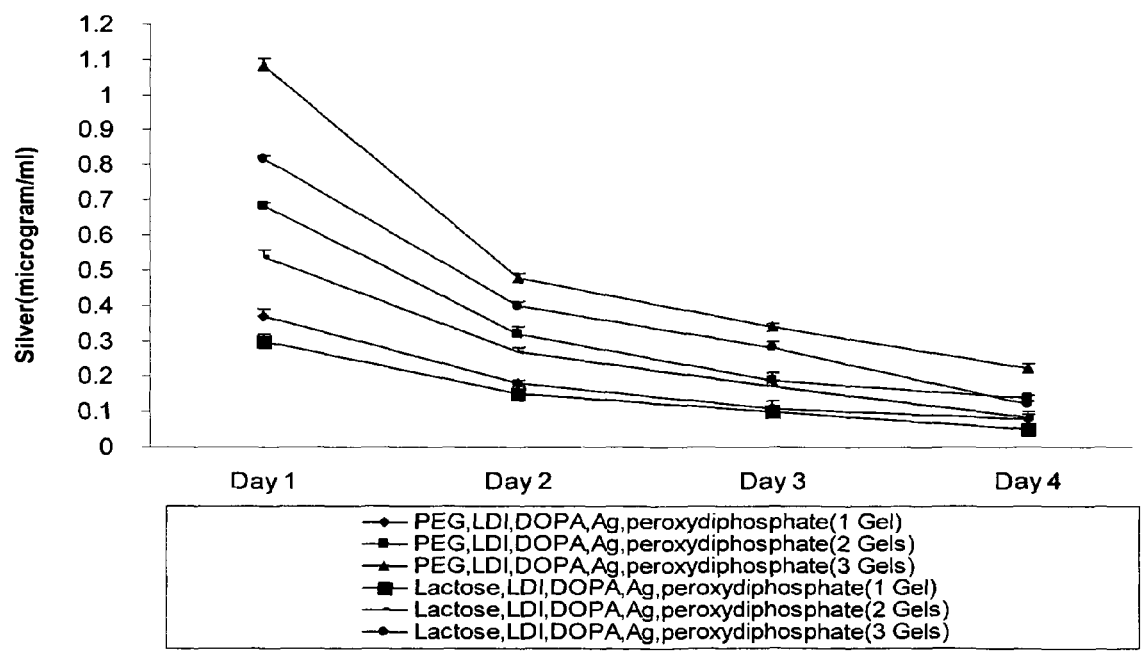
FIG. 20B illustrates silver concentrations in the broth for tubes that were seeded between one and three gels and switched to fresh broth daily for four days.

As can be seen, Ag dissemination from the gels appears to persist for days. When assessed directly, we found that the second day saw 28% of silver leave PEG gels and 23% of Lactose gels, respectively (see FIG. 20B). This dropped subsequently but was still evident on day 4, with 12% and 7% leaving, respectively. The greater leaching from gels placed in fresh media would be consistent with passive diffusion being the driving force of Ag distribution.

Silver ions thus serve the dual functions of catalyzing gelation and providing antimicrobial activity against a broad spectrum of wound contaminating agents. The incorporation of silver within the pre-polymer allows for extended leaching subsequent to gelation of the polymer, with this diffusion presenting the silver akin to current antimicrobial application during surgical interventions. The silver per se presented no adverse impact on cell migration or proliferation. The multifunctional property of silver allows for a simplified polymer that is biocompatible in vitro while being antimicrobial.

In testing the effect of the silver concentration on cell culture, we found that certain concentrations of the silver nitrate exert cytotoxic effects on fibroblasts and endothelial cells which are directly related to the wound-healing process. The result indicated that silver ions greatly inhibited fibroblasts proliferation and prolonged $AgNO_3$ expose produced Ag-dependent cell loss. If human fibroblasts were cultured in a medium with 3 μg/ml of silver nitrate (or higher), 10% of dead cells were found. The cells cultured in a medium with polymer gel cured by the same concentration of the silver nitrate showed more cells survived (only 1 to 2% dead when the polymer cured with 3 μg/ml silver). The concentration of silver in the medium with polymer depends on polymer degradation speed and is lower than that in the medium only at first culture stage.

In general, the optimal concentration of silver for cure time was approximately 17.1 μg/ml. Preferred concentrations of silver for cell proliferation were found to be lower than 15 μg/ml. In general, concentration of silver is preferably in the range of approximately 5 μg/ml to 20 μg/ml. The concentration of silver can also be in the range of 5 μg/ml to 15 μg/ml. These concentration ranges were found to be suitable to catalyze polymerization, were not toxic to mammalian/human cells and exhibited antibacterial effect (that is, functioned as an antibacterial agent) over a period of time in the cured wound healing matrices of the present invention (for example, over a period of a week).

In summary, the present invention provides generally a self-curing (gelation), space-forming gel to ensure wound healing of dermal wounds. The hybrid gels of the present invention limit infections while being non-toxic to the skin cells and not substantially altering normal hemostasis. Polymers of the present invention are readily developed from biocompatible building blocks as described above. The polymers are maintained in a liquid or flowable state by segregating gelation catalysts from the liquid, pre-gel so that the gel could form to the spatial defect of the wound.

Representative gels studied limited proliferation or compromised viability of the two major structural cell types in the skin, dermal fibroblasts and keratinocytes. Cell migration, critical for the ingrowth needed to repair spatial defects, was diminished by both gels. As multiple gel components were responsible, we sought to compensate for these defects by adding a biologically active migration promoter. Collagen I was chosen for its biological and physiochemical properties, not least the fact that it occurs naturally in skin. This protein corrected the migration deficits.

Silver was chosen as a catalyst as it is widely used as a general antimicrobial agent to prevent infections during surgery. We demonstrated that the gels were antimicrobial to a range of skin infection agents including, for example, yeast, aerobic and anaerobic bacteria. Silver both leaves the gel to maintain a relatively aseptic wound bed and remain in the gel to prevent it from becoming a nidus for infection over a four to seven days period (corresponding to the period of initial wound repair during which infection is most likely to occur). Ag was found to leave the PEG gel more efficiently than it left from the lactose gel. Thus, the PEG gel may be preferred in controlling infections in a larger wound bed. However, it is also important to maintain some Ag in the gel, or this can act as a privileged site for an infection nidus, akin to a foreign body. Concentration of various components in the gels of the present invention can be adjusted to optimize results. In both PEG and lactose based gels, at least 20% of the Ag was retained in the gel after one week.

The mechanism of Ag dissemination can impact the antimicrobial actions. Ag appears to diffuse from the gels as the daily leaching was more extensive than the incremental leaching (compare FIG. 20B to FIG. 20A). This leaching was not dependent on gel degradation, as this does not occur extensively in the first week, while the release of Ag was greatest in the first day, when it would be most needed. As such, the Ag would be able to not only diffuse from the gel, but also back into it if infection set in that matrix.

EXPERIMENTAL EXAMPLES

Materials

All reagents in the polymer gel namely polyethylene glycol (PEG), 3,4 dihydroxyphenyl-L-alanine (DOPA), lactose (Lac), silver (Ag), peroxydiphosphate, N-Hydroxysuccinimide (NHS), dicyclohexylcarbodiimide (DCC), methyl trifluoroacetate, 1,1,3,3-tetramethylguanidine (TMG), collagen type I (acid soluble, from kangaroo tail) were obtained from Sigma Chemical Co. (St. Louis, Mo., USA). Lysine diisocyanate methyl ester (LDI) was obtained from Chemical Division, Kyowa Hakko Kogyo Co. Ltd. (Tokyo, Japan). Tissue culture medium was from Life Technologies (Grand Island, N.Y., USA).

Ten microorganisms commonly associated with human skin or wound infections were selected as a challenge. The microorganisms were obtained either from ATCC (Manassus, Va., USA) or from human isolates from the Clinical Microbiology Laboratory of the UPMC Presbyterian/Shadyside Hospital; except *Eschericia coli* and *Acinetobacter baumanii* which were recovered from an actual human wound. *Micrococcus luteus, Staphylococcus aureus* (ATCC 25923), *Streptococcus pyogenes, Diphtheroids, Pseudomonas aeruginosa* (ATCC 27853), *Clostridium perfringens, Bacillus subtilis, Candida albicans* comprise the other eight out of a total of ten organisms tested. The use of PHI-independent clinical isolates and human cells were approved as exempted by the University of Pittsburgh IRB.

Synthesis of Polymers

Synthesis of Lactose-(LDI-DOPA)$_8$ Prepolymer (DLL)

Glassware was dried before use. Lactose 0.70 g (FW 342.3; 2 mmol, —OH 16 mmol) dissolved in 5 ml of dimethyl sulfoxide (DMSO) in a round bottomed flask was flushed with nitrogen. A rubber septum was used to seal the flask. Using a syringe 3.1 ml of LDI (FW 212, d 1.157, 16 mmol, —NCO 32 mmol) was added to the flask. All the constituents in the flask were stirred in the dark at room temperature for 2 days. FT-IR and $^1$H NMR were used in monitoring the isocyanate group consumption and formation of urethane linkages. A solution of DOPA (3.2 g in 20 ml DMSO, FW 197, 16 mmol) was added to the constituents in the flask when the FT-IR showed that 50% of isocyanate groups (peak at 2266 cm$^{-1}$) which were initially present had been consumed. The constituents in the flask were stirred at room temperature for another three days until the FT-IR showed that no more isocyanate groups were present. The product obtained were transferred to dialysis tubing (molecular weight cutoff 1000, Spectrum Laboratories, Inc., Fort Lauderdale, Fla., USA) and dialyzed against three changes of distilled deionized water (DDI water) and dried under vacuum at room temperature. The molecular weight of the product was determined by mass spectrometry. The net DLL pre-polymer obtained was 85.3% pure.

Synthesis of PEG-(LDI-DOPA)$_2$ Prepolymer (DLP)

DLP was synthesized in the same manner as above. In brief 2 g of PEG (FW 400, 10 mmol —OH groups) were reacted with 2 ml of LDI (10 mmol, —NCO 20 mmol) for two days. Subsequently 2 g DOPA (FW 197, 10 mmol, —NH$_2$ 10 mmol) in 20 ml of DMSO was added and reacted at room temperature for three days. The reaction mixture was dialyzed against water and dried under vacuum. The net DLP prepolymer obtained was 81.5% pure.

Synthesis of Glycerol-(LDI-DOPA)$_3$ Prepolymer (DLG)

This prepolymer was generated in a manner similar to that of the DLL material. Here 0.5 g glycerol (FW 92, 5.4 mmol, —OH 16.3 mmol) was dissolved in 5 ml DMSO and reacted with 3.2 ml of LDI (FW 226, d 1.157, 16.38 mmol, —NCO 32.76 mmol) for two days. Then 3.2 g DOPA (FW 197, 16.24 mmol, —NH$_2$ 16.24 mmol) in 20 ml of DMSO was added. The reaction proceeded at room temperature for another three days. The reaction mixture was treated in the same way as that of DLL polymer. The yield of the DLG prepolymer was 83.4%.

Synthesis of PEG-(LDI-DOPA)$_2$ Prepolymer (DLP) with Collagen

Glassware was dried in a vacuum oven prior to use. 2 g PEG were reacted with 2 ml of LDI (FW 226, d 1.157, 10.75 mmol, —NCO 21.5 mmol) for two days, then 2 g DOPA in 20 ml of DMSO were added (at this point, the reaction mixture was not clear). The reaction was performed at room temperature for three days until the reaction mixture was clear and FT-IR showed no remaining isocyanate groups. Then, N-hydroxysuccinimide (1.15 g, 10 mmol) and 2.06 g dicyclohexylcarbodiimide were added. The reaction mixture was stirred at room temperature for 20 hr. Dicyclohexylurea was removed by centrifugation (3000 rpm for 30 min). The supernatant was transferred to a flask and 0.1 g collagen I (from Bovine) was added. The reaction mixture was stirred at room temperature for 10 hours, then, transferred to dialysis tubing (Spectrum Laboratories, Inc., Fort Lauderdale, Fla., USA, molecular weight cutoff of 1000). The products were dialyzed against DDI water to remove DMSO and small molecular weight monomers (water changed every three hours) until a precipitate appeared. The precipitate was dissolved with 0.1 M $Na_2B_4O_7$ and the solution was initiated by $AgNO_3/K_4P_2O_8$ to make gel.

Synthesis of Dopa-Collagen Prepolymer

Preparation of N-trifluoroacetyl-L-DOPA 1.97 g L-DOPA (10 mmol) and 5 ml of dry methanol was added into an oven-dried 25 ml round-bottomed flask equipped with a Teflon stirring bar and rubber septum and purged with dry argon. Then, 1.3 ml of TMG (10 mmol) and 1.4 ml of methyl trifluoroacetate (12.5 mmol) was added. The mixture was stirred vigorously at room temperature until DOPA had completely dissolved (after about 24 hr). At this point, the flask was immersed in cold water (0° C.) and 5 ml of methanol and 4 g Dowex 50 resin ($H^+$ form) were added. The mixture was filtered after stirring for 10 min. The filtrate was evaporated under reduced pressure. The crude product was re-crystallized from ethyl acetate and the yield of N-trifluoroacetyl-L-DOPA was 78%. See Curphey, T. J. Trifluoroacetylation of amino acids and peptides by ethyl trifluoroacetate. *J. Org. Chem.* 1979, 44, 2805-2807; Lapidot, Y.; Rappoport, S.; Wolman, Y. Use of ester of N-hydroxysuccinimide in the synthesis of N-acrylamino acids. *J. Lipid Research* 1967, 8, 142-145.

Preparation of Activated L-DOPA

L-DOPA was activated by reacting N-trifluoroacetyl-L-DOPA obtained above (2.93 g, 10 mmol) with N-hydroxysuccinimide (1.15 g, 10 mmol) in the presence of 50 ml dry ethyl acetate and 2.06 g dicyclohexylcarbodiimide. See Rothe, M.; Falanga, V. Growth factors. Their biology and promise in dermatologic diseases and tissue repair. *Arch. Dermatol.* 1989, 125, 1390-1398. The reaction mixture was stirred at room temperature for 20 hr. Dicyclohexylurea was removed by filtration. The filtrate was concentrated under reduced pressure to yield white crystals of N-trifluoroacetyl-L-DOPA hydroxysuccinimide ester 2.2 g (76%).

Isolation of Acid Soluble Collagen from Rat Skin

Acid soluble type I collagen was extracted from rat skin by the method described by Piez et al. Rat skin samples were delicately cleaned of hair residues with a sharp razor blade, and subcutaneous fat was washed with ether. See Piez, K. A.; Eigner, E. A.; Lewis, M. S. The chromatographic separation and amino acid composition of the subunits of several collagens. *Biochemistry* 1963, 2, 58-66. Treated skin samples (0.5 g) were minced with scissors into small pieces (1×1 mm each), and placed in 100 ml of 0.5 mol/L ice-cold acetic acid solution at 4° C. for 48 hr with constant shaking. The mixture was finely homogenized for 60 s. Pepsin was added (1 g/L) to the suspension, and digestion lasted 16 hr at 4° C. with constant shaking. The digested homogenate was centrifuged at 30,000×g for 60 min at 4° C. The suspension was collected and the pellet was re-digested and centrifuged under the same conditions. Collagen was precipitated from the suspension by adding sodium chloride to 2.2 M. After stirring for 2 hr at 4° C., the precipitate was collected by centrifugation at 30,000×g for 30 min. The collagen was re-suspended in 50 ml of 0.5 mol/L acetic acid and kept shaking over night at 4° C. The solution was dialyzed against 0.5 M acetic acid at 4° C. for 3 days with 6 changes. This salt-free collagen was freeze dried and stored over calcium chloride at 4° C.

Conjugation of L-DOPA to Collagen 200 mg activated L-DOPA (N-trifluoroacetyl-L-DOPA hydroxysuccinimide ester) reacted with 20 ml of collagen solution (1 mg/ml) in PBS buffer (pH 5) for two days at room temperature with constant stirring.[13] See Myles, J. L.; Burgess, B. T.; Dickinson, R. B. Modification of the adhesive properties of collagen by covalent grafting with RGD peptides. *J. Biomater. Sci. Polymer Edn.* 2000, 11, 69-86. N-hydroxysuccinimide on activated L-DOPA formed stable amide bonds with primary amine groups on collagen. Excess activated L-DOPA and other chemicals were removed by dialysis against water. Water was changed every 3 hours until Kaiser test showed negative in the dialysate. DOPA conjugated collagen was freeze dried and stored at 4° C.

Deprotection of DOPA-Modified Collagen 100 mg DOPA-conjugated collagen obtained by above treatment was put in 10 ml of THF at room temperature. 10 ml of 0.4 M sodium hydroxide solution was added and the mixture was stirred at room temperature for 16 hour. The product was put into a dialysis bag and dialyzed with water to remove small molecules including methyl trifluoroacetate and sodium hydroxide. Water was changed every 3 hours until neutral pH appeared in dialysis solution. Thus, DOPA-modified without N-protected collagen was obtained.

Preparation of the Polymer Gels

The DOPA containing polymer gels were prepared by radical polymerization of an aqueous solution of prepolymer using the redox initiation system Ag+/potassium peroxydiphosphate. 50 µl of $AgNO_3/K_4P_2O_8$ solution (various loadings) were added to 7 ml of prepolymer solution (0.3 g prepolymer dissolved in 1 ml of 0.1 M $Na_2B_4O_7$ solution) in a 75 mm teflon dish.

Polymer Degradation In Vitro

Polymer degradation was tested in vitro by placing known amounts of polymer gel in phosphate buffer solution (1×PBS; 100 mg polymer/ml PBS) at 37° C. for up to three weeks. The concentration of DOPA liberated from the polymer was detected by UV-VIS as described by Waite et al. See Waite J H, Benedict C V. Assay of dihydroxyphenylalanine (dopa) in invertebrate structural proteins. Methods Enzymol 1984; 107:397-413. The changes in pH of the solution due to polymer degradation were assessed in parallel samples with the use of a pH meter.

Swelling Property of Polymer Gels

The determination of swelling characteristics of polymer gels was determined at 37° C. using a gravimetric method. See Arica M Y, Bayramoglu G, Arica B, Yalcin E, Ito K, Yagci Y. Novel hydrogel membrane based on copoly(hydroxyethyl methacrylate/pvinylbenzyl-poly(ethylene oxide)) for biomedical applications: properties and drug release characteristics. Macromol Biosci 2005; 5(10):983-92; Andreopoulos F M, Beckman E J, Russell A J. Light-induced tailoring of PEG-hydrogel properties. Biomaterials 1998; 19(15):1343-52. The dry gels were weighed at first and then immersed in a phosphate buffer solution at a pH 7.4. At different time points the swollen gels were removed from the buffer and weighed on a sensitive balance. The swelling ratio was calculated as follows $$\text{Swelling ratio (\%)}=[(W_s-W_d)/W_d]\times 100$$

Where $W_s$ and $W_d$ stand for swollen and dry weights of the gels respectively. The change in the diameter of the gel at various time points was also determined.

Microbial Analysis

Disc Diffusion Assay

Initially, we tested the antimicrobial properties by a modification of the disc diffusion method. This provided a measure of both the antimicrobial activity and diffusibility of the gelated Ag. See Gallant-Behm C L, Yin H Q, Liu S, Heggers J P, Langford R E, Olson M E, et al. Comparison of in vitro disc diffusion and time kill-kinetic assays for the evaluation of antimicrobial wound dressing efficacy. Wound Repair Regen 2005; 13(4):412-21.

The control 'disc', was filter paper (Schleicher and Schuell Co., Keene, N.H. USA), 1.25 cm diameter size and 1 mm thickness, which was impregnated with 20 microliter of 1% silver nitrate solution for a final mass of 0.125 µg Ag. Test 'discs' were cut from polymerized matrix, 2 cm diameter in size and 1 mm in thickness. In the prepolymer solution we had 10 microgram/microliter of Ag for a final load of 3.3 µg/disc.

The stock microbial cultures were plated onto the blood agar plates and colonies were picked manually. They were suspended in trypticase soy broth (BD Diagnostics, Sparks, Md., USA) to obtain an equivalent to 0.5 Mcfarland barium Sulphate ($10^7$-$10^8$ CFU/ml) standard. A sterile cotton swab was suspended in the microbe-containing trypticase soy broth and used to streak at right angles in four directions in blood agar plates to form a confluent lawn of growth on 150 mm plates of Mueller-Hinton agar with sheep blood (BD Diagnostics, Sparks, Md.). Test and control discs were placed on the plates which were incubated at 37° C. for 24 hours. The zone of inhibition surrounding the control as well as our experimental gels was measured. For anaerobic organisms the inoculated plates were placed into a sealed anaerobic bag (AnaBag 150) (Hardy Diagnostics, Santa Maria, Calif., USA) containing an anaerobic generator sachet (Anaerogen) (Gibson Laboratories Inc., Lexington, Ky., USA). The anaerobic cultures were incubated for 48 hours at 25° C. For each experiment, a similar plate inoculated with *Micrococcus luteus* served as a control.

Microbicidal and Microbiostatic Assays

To distinguish whether the microbial inhibitions noted in the disc diffusion method were due to bactericidal or bacteriostatic effects, quantitative assays were employed taking into consideration the aerobes, anaerobes and yeast. See Gallant-Behm C L, Yin H Q, Liu S, Heggers J P, Langford R E, Olson M E, et al. Comparison of in vitro disc diffusion and time kill-kinetic assays for the evaluation of antimicrobial wound dressing efficacy. Wound Repair Regen 2005; 13(4): 412-21; Wright J B, Lam K, Hansen D, Burrell R E. Efficacy of topical silver against fungal burn wound pathogens. Am J Infect Control 1999; 27(4):344-50; Bowler P G, Duerden B I, Armstrong D G. Wound microbiology and associated approaches to wound management. Clin Microbiol Rev 2001; 14(2):244-69.

The suspension of the microorganism was made by first allowing the organism to grow in appropriate broth. For all the microorganisms except *S. pyogenes, S. aureus* and *C. perfringens*, Mueller Hinton Broth (BD Diagnostics, Sparks, Md., USA) was used. For *S. pyogenes* and *S. aureus* Todd Hewitt Broth (BD Diagnostics, Sparks, Md., USA) was used. For *C. perfringens* trypticase soy broth was being used. The growth was adjusted to a 0.5 Mcfarland Standard ($10^7$-$10^8$ CFU/ml) and a 1/200 dilution of this broth was made ($10^5$-$10^8$ CFU/ml) using saline as a diluent. For each assay, four tubes, each containing 4 ml of broth were used. One tube contained one disc of the gel under test which was 1.3 cm in diameter and 1 mm in thickness with the final load of Ag being 2.58 ug. The second tube contained two discs of the gel, a third tube contained three discs. The fourth tube contained no gel and served as a growth control. To each of the four tubes, 0.1 ml of the diluted bacterial suspension was added.

For *C. perfringens*, a 1/100 dilution of the standardized suspension was used as the inoculum. Aerobes were incubated at 37° C. for 24 hours whereas anaerobes were incubated at 25° C. for 48 hours. Before incubation, the actual size of the inoculum was determined by making serial dilutions from the inoculated growth control tube. One tenth ml of these dilutions were inoculated in triplicate onto blood agar plates (BD Diagnostic Systems, Sparks, Md.) which were incubated overnight at 37° C. After incubation of the tubes, similar dilutions were made and plated to determine the fraction of the original inoculum that survived.

Atomic Absorption Spectroscopy

Quantitative measurement of the Ag both retained in and leaving from the gel would suggest temporal nature of the antimicrobial activities. Kumar R, Munstedt H. Silver ion release from antimicrobial polyamide/silver composites. Biomaterials 2005; 26(14):2081-8; Dowsett C. The use of silver-based dressings in wound care. Nurs Stand 2004; 19(7):56-60. Total leaching of Ag from gels was assessed by placing a 1.3 cm diameter, 1 mm thick piece of gel in trypticase soy broth for 10 days having a final load of Ag 2.58 µg. In addition, the daily leaching of silver was assessed by moving gels from tube to tube of trypticase soy broth at 24 hr intervals. Ag concentration was determined by atomic absorption spectroscopy using a Perkin-Elmer EDLS (Perkin Elmer AA5100, Wellesley, Mass., USA).

Dermal Fibroblast and Keratinocyte Functioning

The gels were assessed for biocompatibility by determining effects on survival, proliferation and migration of human dermal cells and keratinocytes. Primary human dermal fibroblasts were obtained from Musculoskeletal Research center, Department of Orthopaedic Surgery, University of Pittsburgh Medical center, Pittsburgh, Pa., USA. For human keratinocytes we used HaCaT cells, a spontaneously immortalized, but not transformed human keratinocyte cell-line which was provided by Dr. N. Fusenig German Cancer Research Center (Heidelberg, Germany). These studies were deemed exempted (4e) by the University of Pittsburgh IRB.

The primary human dermal fibroblasts and keratinocytes were subcultured into 24 well plates at 20,000 per well. When the cells became 70% confluent the gel additive was placed along with 1 ml of complete medium. Solid gels were 1 mm thick and cut to 90% of the well surface (9 mm diameter); Liquid gels were of the same solution used for the solid gel but for the initiators, and added to cover the well surface completely. Cell viability was assessed at 24, 48 and 72 hours by MTT Assay and cell proliferation by automated Coulter Counter (Beckman Coulter Instruments). For cell migration, an in vitro wound healing assay was performed.

Hemostasis Assessments

As the gel matrix will be placed into wounds with blood, it needs to be either hemostatic or not interfere with the normal hemostasis. Otani Y, Tabata Y, Ikada Y. Hemostatic capability of rapidly curable glues from gelatin, poly(L-glutamic acid) and carbodiimide. Biomaterials 1998; 19(22):2091-8. Excess human blood, citrated blood and platelet-poor plasma, were used as approved by the University of Pittsburgh IRB (exemption 4e). Prothrombin time, activated partial thromboplastin time, clotting time were measured by using tube method with reagents from BioData Corp. (Horsham, Pa., USA).

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A composition comprising:
   (a) at least one biologically active agent selected from the group of a protein, an organic catalyst, a ribozyme, an organometallic, a glycoprotein, a glycosaminoglycan, a peptide, a polyamine, a polyamino acid, an antibody, a nucleic acid, a steroidal molecule, an antibiotic, an antiviral, an antimycotic, an anticancer agent, an analgesic agent, an antirejection agent, an immunosuppressant, a cytokine, a carbohydrate, an oleophobic, a lipid, extracellular matrix, a component of extracellular matrix, a growth factor, a hemostatic agent, a virus, a virus vector and a prion, and (b) a polymerizing molecule selected from the group consisting of dihydroxyphenyl-L-alanine (DOPA) and derivatives thereof, histidine and derivatives thereof; lysine and derivatives thereof, tryptophan and derivatives thereof, tyrosine and derivatives thereof, and combinations thereof, covalently bonded to the biologically active agent, wherein the composition polymerizes by free radical polymerization of at least one functional group of the polymerizing molecule upon initiation to form a biodegradable polymer.

2. The composition of claim 1 wherein the polymerizing molecule is dihydroxyphenyl-L-alanine (DOPA) or a derivative of dihydroxyphenyl-L-alanine.

3. The composition of claim 1 wherein the polymerizing molecule is dihydroxyphenyl-L-alanine (DOPA).

4. The composition of claim 1 wherein the biologically active agent is collagen or a growth factor.

5. The composition of claim 3 wherein the biologically active agent is collagen or a growth factor.

6. The composition of claim 5 wherein the biologically active agent is extracellular matrix comprising collagen.

7. The composition of claim 1 wherein the biologically active agent comprises collagen.

8. The composition of claim 1 further comprising a synthetic component prepared by reacting:

(a) at least one multi-isocyanate functional conjugate comprising the reaction product of a core molecule having reactive hydrogen groups and at least one multi-isocyanate functional molecule wherein the core molecule is selected from the group of glycerol, diglycerol, ascorbic acid, a saccharide, pentaerythritol, xylitol, arabitol, fucitol, ribitol, gluconic acid, glucosamine, sorbitol, mannitol, a steroid, a biocompatible multi-functional polymer or combinations thereof and (b) a polymerizing molecule that is adapted to undergo a free radical polymerization, the polymerizing molecule selected from the group consisting of dihydroxyphenyl-L-alanine (DOPA) and derivatives thereof, histidine and derivatives thereof, lysine and derivatives thereof, tryptophan and derivatives thereof, tyrosine and derivatives thereof, and combinations thereof.

9. The composition of claim 1 further comprising an initiating component adapted to initiate free radical polymerization.

10. The composition of claim 9 wherein the initiating component comprises silver or a silver compound.

11. The composition of claim 10 wherein the initiating component further comprises peroxydiphosphate.

12. The composition of claim 8 further comprising an initiating component adapted to initiate free radical polymerization.

13. The composition of claim 12 wherein the initiating component comprises silver or a silver compound.

14. The composition of claim 13 wherein the initiating component further comprises peroxydiphosphate.

15. The composition of claim 10 wherein the concentration of silver or of the silver compound is suitable such that the silver or the silver compound functions as an antimicrobial agent.

16. The composition of claim 15 wherein the concentration of silver or of the silver compound is in the range of approximately 5 µg/ml to 20 µg/ml based upon the volume of uncured components of the composition.

17. The composition of claim 15 wherein the silver or the silver compound persists within a polymeric network formed from the composition in an antimicrobial level for at least one week in a wound.

18. The composition of claim 1 wherein the biologically active agent is selected from the group consisting of a protein, a glycoprotein, a glycosaminoglycan, a peptide, a carbohydrate, extracellular matrix, a component of extracellular matrix, a growth factor, and a hemostatic agent.

19. The composition of claim 8 wherein the biologically active agent comprises extracellular matrix or a component of extracellular matrix.

20. The composition of claim 1 wherein the biologically active agent comprises a hemostatic surface.

21. The composition of claim 20 wherein the hemostatic surface agent comprises collagen, fibrin or plasmin.

22. The composition of claim 1 wherein the biologically active agent comprises a growth factor.

23. The composition of claim 22 wherein the growth factor is EGF, TGFa, PDGF, VEGF, IGF-1, FGF, HGF, KGF, TGFb, a CXCR3 ligand, IL-10 or IL-4.

24. The composition of claim 22 wherein the growth factor is VEGF, EGF, TGFa, FGFs, TGFb, IGF or PDGF.

25. The composition of claim 1 wherein the biologically active agent comprises a hemostatic agent.

26. The composition of claim 25 wherein the hemostatic agent is ATP, a derivative of ATP, epinephrine or a derivative of epinephrine.

27. The composition of claim 1 wherein the biologically active agent comprises an agent selected to promote at least one of cell adhesion, cell proliferation or cell migration.

28. The composition of claim 27 wherein the biologically active agent comprises sites for binding of at least one of beta1 or beta3 integrins.

29. The composition of claim 1 wherein the biologically active agent comprises an analgesic agent.

30. The composition of claim 27 wherein the analgesic agent is a topical anesthetic.

31. The composition of claim 1 wherein the biologically active agent comprises an antimicrobial agent.

32. The composition of claim 1 wherein the antimicrobial agent is a macrolide, a topoisomerase inhibitors or a cephalosporin.

33. The composition of claim 8 wherein the core molecule is selected from the group of glycerol, diglycerol, ascorbic acid, a saccharide, pentaerythritol, xylitol, arabitol, fucitol, ribitol, gluconic acid, glucosamine, sorbitol, mannitol, a steroid, a biocompatible multi-functional polymers or combinations thereof.

34. The composition of claim 33 wherein the core molecule is selected from the group consisting of glycerol, ascorbic acid, lactose, glucose, polyethylene glycol, and combinations thereof.

35. The composition of claim 8 wherein the multi-isocyanate functional molecule that reacts with the core molecule is selected from the group consisting of lysine di-isocyanate, a lysine di-isocyanate derivative, lysine tri-isocyanate, a derivative of lysine tri-isocyanate, putrescine and combinations thereof.

36. The composition of claim 8 wherein the polymerizing molecule that reacts with the conjugate to form the synthetic component is dihydroxyphenyl-L-alanine (DOPA) a derivative of dihydroxyphenyl-L-alanine (DOPA), histidine, a derivative of histidine, lysine, a derivative of lysine, tryptophan, a derivative of tryptophan, tyrosine or a derivative of tyrosine.

37. The composition of claim 8 wherein the polymerizing molecule that reacts with the conjugate to form the synthetic component is dihydroxyphenyl-L-alanine (DOPA).

38. The composition of claim 8 wherein:
(a) the core molecule is selected from the group consisting of glycerol, ascorbic acid, lactose, glucose, polyethylene glycol, and combinations thereof;
(b) the multi-isocyanate functional molecule is selected from the group consisting of lysine diisocyanate and derivatives thereof, lysine triisocyanate and derivatives thereof, and combinations thereof; and
(c) the polymerizing molecule that reacts with the conjugate to form the synthetic component comprises dihydroxyphenyl-L-alanine.

39. The composition of claim 1 further comprising a free biologically active agent.

40. The composition of claim 11 further comprising a free biologically active agent.

41. A composition comprising a first component comprising (i) at least one biologically active agent covalently attached to a first polymerizing molecule that undergoes a free radical polymerization upon initiation via at least on functional group of the first polymerizing molecule, and (ii) a second component formed by reacting (a) at least one core molecule having reactive hydrogen groups with at least one multi-isocyanate functional molecule to form a conjugate comprising isocyanate groups and (b) a second polymerizing molecule that undergoes a free radical polymerization via at least one functional group of the second polymerizing molecule, the second polymerizing molecule including at least one reactive hydrogen to react with the isocyanate groups of the conjugate, the composition polymerizing via free radical polymerization upon initiation,
wherein the biologically active agent is selected from the group consisting of a protein, an organic catalyst, a ribozyme, an organometallic, a glycoprotein, a glycosaminoglycan, a peptide, a polyamine, a polyamino acid, an antibody, a nucleic acid, a steroidal molecule, an antibiotic, an antiviral, an antimycotic, an anticancer agent, an analgesic agent, an antirejection agent, an immunosuppressant, a cytokine, a carbohydrate, an oleophobic, a lipid, extracellular matrix, a component of extracellular matrix, a growth factor, a hemostatic agent, a virus, a virus vector and a prion,
wherein the first polymerizing molecule and the second polymerizing molecule are independently selected from the group consisting of dihydroxyphenyl-L-alanine (DOPA) and derivatives thereof, histidine and derivatives thereof lysine and derivatives thereof, tryptophan and derivatives thereof, tyrosine and derivatives thereof, and combinations thereof,
and wherein the core molecule is selected from the group consisting of glycerol, diglycerol, ascorbic acid, saccharides, pentaerythritol, xylitol, arabitol, fucitol, ribitol, gluconic acid, glucosamine, sorbitol, mannitol, a steroid, a biocompatible multi-functional polymer and combinations thereof.

42. The composition of claim 41 wherein the first polymerizing molecule and the second polymerizing molecule are dihydroxyphenyl-L-alanine (DOPA).

43. The composition of claim 42 wherein the biologically active agent is selected from the group consisting of a protein, a glycoprotein, a glycosaminoglycan, a peptide, a carbohydrate, extracellular matrix, a component of extracellular matrix, a growth factor, and a hemostatic agent.

44. The composition of claim 42 wherein the biologically active agent comprises collagen.

* * * * *